(12) United States Patent
Ogino et al.

(10) Patent No.: US 12,348,853 B2
(45) Date of Patent: *Jul. 1, 2025

(54) IMAGING SYSTEM, IMAGING METHOD, CONTROL APPARATUS, COMPUTER PROGRAM AND RECORDING MEDIUM

(71) Applicant: NEC Corporation, Tokyo (JP)

(72) Inventors: Yuka Ogino, Tokyo (JP); Keiichi Chono, Tokyo (JP)

(73) Assignee: NEC CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/638,867

(22) Filed: Apr. 18, 2024

(65) Prior Publication Data

US 2024/0267610 A1    Aug. 8, 2024

Related U.S. Application Data

(63) Continuation of application No. 17/619,769, filed as application No. PCT/JP2019/024068 on Jun. 18, 2019, now Pat. No. 11,997,377.

(51) Int. Cl.
*H04N 23/611* (2023.01)
*G06T 7/70* (2017.01)
(Continued)

(52) U.S. Cl.
CPC ............ *H04N 23/611* (2023.01); *G06T 7/70* (2017.01); *G06V 40/19* (2022.01); *H04N 23/667* (2023.01);
(Continued)

(58) Field of Classification Search
CPC .... H04N 23/611; H04N 23/667; H04N 23/67; H04N 23/90; H04N 23/45; G06T 7/70; G06T 2207/30201; G06T 1/00; G06V 40/19; G06V 40/166; A61B 5/1113; A61B 5/1171; G03B 15/00; G03B 19/07
See application file for complete search history.

(56) References Cited

U.S. PATENT DOCUMENTS

| 5,947,230 A | 9/1999 | Ohta |
| 8,243,133 B1 | 8/2012 | Northcott ............... G06V 40/19 348/78 |

(Continued)

FOREIGN PATENT DOCUMENTS

| CN | 103516976 A | 1/2014 |
| JP | H10-159529 A | 6/1998 |

(Continued)

OTHER PUBLICATIONS

International Search Report for PCT Application No. PCT/JP2019/024068, mailed on Sep. 3, 2019.

(Continued)

*Primary Examiner* — Michael E Teitelbaum

(57) ABSTRACT

An imaging system is provided with: a first imaging apparatus (2) that captures an image of an imaging target (T, TP) that is located at a first point (P1); a second imaging apparatus (3) a focus position of which is set at a second point (P2) that is located at a forward side along a moving direction of the imaging target than the first point; and a control apparatus (6) that controls the second imaging apparatus to capture an image of the imaging target that is located at the second point on the basis of the image (200) captured by the first imaging apparatus.

9 Claims, 10 Drawing Sheets

(51) Int. Cl.
    *G06V 40/19*     (2022.01)
    *H04N 23/667*     (2023.01)
    *H04N 23/67*     (2023.01)
    *H04N 23/90*     (2023.01)

(52) U.S. Cl.
    CPC ............. *H04N 23/67* (2023.01); *H04N 23/90* (2023.01); *G06T 2207/30201* (2013.01)

(56) References Cited

U.S. PATENT DOCUMENTS

| | | | |
|---|---|---|---|
| 10,459,103 B1 | 10/2019 | Shi | G06V 3/08 |
| 2005/0084179 A1 | 4/2005 | Hanna et al. | |
| 2006/0221229 A1 | 10/2006 | Ogawa et al. | |
| 2007/0092245 A1 | 4/2007 | Bazakos | G06V 40/166 |
| | | | 396/427 |
| 2011/0222725 A1 | 9/2011 | Mitsushio et al. | |
| 2013/0342752 A1 | 12/2013 | Sugawara | |
| 2019/0362059 A1 | 11/2019 | Xin | G06V 40/172 |

FOREIGN PATENT DOCUMENTS

| | | |
|---|---|---|
| JP | 2006-130325 A | 5/2006 |
| JP | 2006-163683 A | 6/2006 |
| JP | 2006-309742 A | 11/2006 |
| JP | 2007-504562 A | 3/2007 |
| JP | 2007-082655 A | 4/2007 |
| JP | 2010-134735 A | 6/2010 |
| JP | 2011-211678 A | 10/2011 |
| JP | 2013-045249 A | 3/2013 |
| JP | 2014-067090 A | 4/2014 |
| WO | 2009/016846 A1 | 2/2009 |
| WO | 2018/133282 A1 | 7/2018 |

OTHER PUBLICATIONS

Extended European Search Report for EP Application No. EP19933805.4 dated on May 3, 2022.
Chinese Office Action for CN Application No. 201980097552. X, mailed on Feb. 9, 2023 with English Translation.
JP Office Action for JP Application No. 2022-192948, mailed on Oct. 31, 2023 with English Translation.
SG Office Action for SG Application No. 11202113985U , mailed on Dec. 12, 2023.

IMAGING SYSTEM, IMAGING METHOD, CONTROL APPARATUS, COMPUTER PROGRAM AND RECORDING MEDIUM

This application is a continuation application of U.S. patent application Ser. No. 17/619,769 filed on Dec. 16, 2021, which is a National Stage Entry of PCT/JP2019/024068 filed on Jun. 18, 2019, the contents of all of which are incorporated herein by reference, in their entirety.

TECHNICAL FIELD

This disclosure relates to a technical field of an imaging system, an imaging method, a control apparatus, a computer program and a recording medium that are configured to capture an image of an imaging target.

BACKGROUND ART

An iris authentication system that performs an iris authentication by capturing an image of an iris of a target person that is one example of an imaging target is known as one example of an imaging system that is configured to capture an image of the imaging target. For example, a Patent Literature 1 discloses an iris authentication in a walk-through type that is configured to enable the iris authentication even when the target person does not stop. Specifically, the Patent Literature 1 discloses the iris authentication system that is provided with a wide angle camera and a plurality of iris cameras and that selects, from the plurality of iris cameras, the iris camera that should be used for the authentication by processing an image of the wide angle camera.

In addition, there are Patent Literatures 2 and 3 as a background art document relating to this disclosure.

CITATION LIST

Patent Literature

Patent Literature 1: JP2010-134735A1
Patent Literature 2: JP2014-067090A1
Patent Literature 3: JPH10-159529A1

SUMMARY OF INVENTION

Technical Problem

The iris authentication system disclosed in the Patent Literature 1 has such a technical problem that there is a possibility that it is not able to capture the image of the moving target person properly by using the iris camera. Specifically, the iris authentication system that is provided with the wide angle camera and the plurality of iris cameras is required to select the iris camera that should be used for the authentication (furthermore, set a parameter of the selected iris camera, if needed) before the moving target person reaches a focus position of the iris camera. Thus, it is desired that the iris authentication system capture the image of the target person by using the wide angle camera before the moving target person reaches the focus position of the iris camera and select the iris camera that should be used for the authentication on the basis of the image of the wide angle camera. However, the Patent Literature 1 does not consider this point.

Note that there is a possibility that the above described technical problem occurs in not only the iris authentication system but also any imaging system that controls a second imaging apparatus to capture an image of a moving imaging target on the basis of an image of the imaging target captured by a first imaging apparatus.

It is therefore an example object of this disclosure to provide an imaging system, an imaging method, a control apparatus, a computer program and a recording medium that can solve the above described technical problem. By way of example, an example object of this disclosure is to provide an imaging system, an imaging method, a control apparatus, a computer program and a recording medium that can capture an image of a moving imaging target properly.

Solution to Problem

A first example aspect of an imaging system for solving the technical problem is provided with: a first imaging apparatus that captures an image of an imaging target that is located at a first point; a second imaging apparatus a focus position of which is set at a second point that is located at a forward side along a moving direction of the imaging target than the first point; and a control apparatus that controls the second imaging apparatus to capture an image of the imaging target that is located at the second point on the basis of the image captured by the first imaging apparatus.

A second example aspect of an imaging system for solving the technical problem is provided with: an imaging apparatus a state of which is switchable between a first state and a second state, that captures an image of an imaging target that is located at a first point in the first state, and that captures an image of the imaging target that is located at a second point, which is located at a forward side along a moving direction of the imaging target than the first point, in the second state; and a control apparatus that switches the imaging apparatus from the first state to the second state by controlling the imaging apparatus on the basis of the image captured by the imaging apparatus in the first state.

A first example aspect of an imaging method for solving the technical problem includes: an obtaining step that obtains an image captured by a first imaging apparatus that captures an image of an imaging target that is located at a first point; and a controlling step that controls, on the basis of the image obtained at the obtaining step, a second imaging apparatus a focus position of which is set at a second point to capture an image of the imaging target located at the second point that is located at a forward side along a moving direction of the imaging target than the first point.

A second example aspect of an imaging method for solving the technical problem includes: an obtaining step that obtains an image captured by an imaging apparatus in a first state from the imaging apparatus a state of which is switchable between the first state and a second state, that captures an image of an imaging target that is located at a first point in the first state, and that captures an image of the imaging target that is located at a second point, which is located at a forward side along a moving direction of the imaging target than the first point, in the second state; and a controlling step that switches the imaging apparatus from the first state to the second state by controlling the imaging apparatus on the basis of the image obtained at the obtaining step.

A first example aspect of a control apparatus for solving the technical problem is provided with: an obtaining unit that obtains an image captured by a first imaging apparatus that captures an image of an imaging target that is located at a first point; and a controlling unit that controls, on the basis of the image obtained by the obtaining unit, a second imaging apparatus a focus position of which is set at a second point to capture an image of the imaging located at the second point that is located at a forward side along a moving direction of the imaging target than the first point.

A second example aspect of a control apparatus for solving the technical problem is provided with: an obtaining unit that obtains an image captured by an imaging apparatus in a first state from the imaging apparatus a state of which is switchable between the first state and a second state, that captures an image of an imaging target that is located at a first point in the first state, and that captures an image of the imaging target that is located at a second point, which is located at a forward side along a moving direction of the imaging target than the first point, in the second state; and a controlling unit that switches the imaging apparatus from the first state to the second state by controlling the imaging apparatus on the basis of the image obtained by the obtaining unit.

One example aspect of a computer program for solving the technical problem allows a computer to perform the first or second example aspect of the imaging method described above.

One example aspect of a recording medium for solving the technical problem is a recording medium on which the one example aspect of the computer program described above is recorded.

Advantageous Effects of Invention

According to the example aspect of each of the imaging system, the imaging method, the control apparatus, the computer program and the recording medium described above, it is possible to capture an image of a moving imaging target properly.

DESCRIPTION OF EXAMPLE EMBODIMENTS

Hereinafter, an example embodiment of an imaging system, an imaging method, a control apparatus, a computer program and a recording medium will be described with reference to the drawings. The following describes an iris authentication system 1 to which the example embodiment of the imaging system, the imaging method, the control apparatus, the computer program and the recording medium is applied. The iris authentication system 1 performs an iris authentication operation for performing an authentication of an authentication target person T on the basis of a pattern of an iris of the authentication target person T that is one example of an imaging target. The iris authentication system 1 may be used as a part of a system for automating an immigration procedure in an airport (what we call ABC (Automated Border Control)). In this case, the iris authentication system 1 may be an iris authentication system in a walk-through type that performs the authentication of moving authentication target person T. In the below described description, an example in which the iris authentication system 1 is the iris authentication system in the walk-through type will be described. However, the iris authentication system 1 is not limited to the iris authentication system that is described in this paragraph as one example, and may be used as any iris authentication system that is configured to perform the authentication of the authentication target person T. Note that the iris authentication system 1 is one example of an "imaging system" in a supplementary note described below.

(1) CONFIGURATION OF IRIS AUTHENTICATION SYSTEM 1

(1-1) Entire Configuration of Iris Authentication System 1

Figure 1:
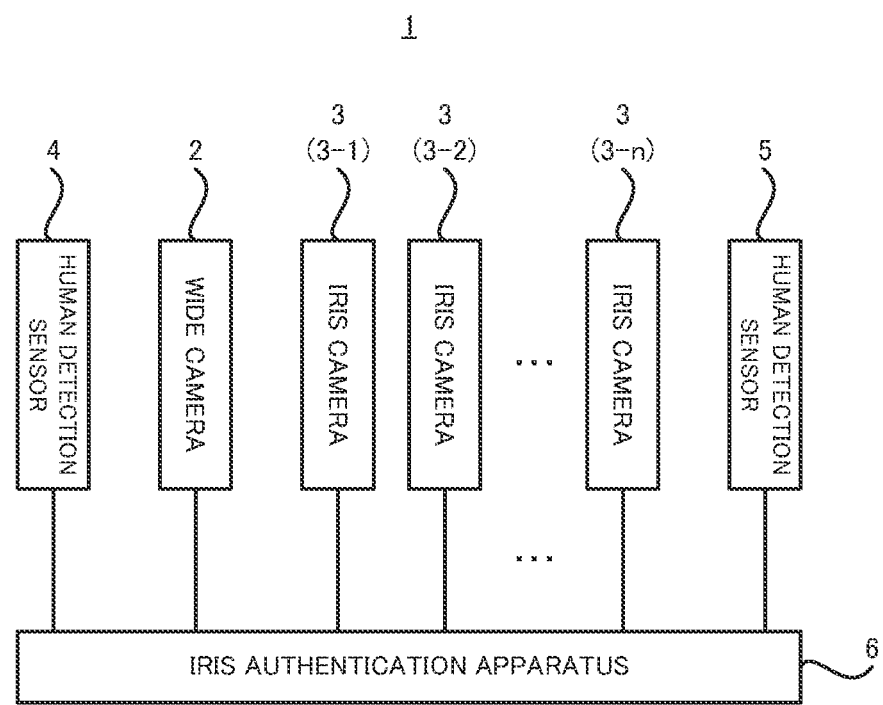
FIG. 1 is a block diagram that illustrates an entire configuration of an iris authentication system in the present example embodiment.

Firstly, with reference to FIG. 1, an entire configuration of the iris authentication system 1 in the present example embodiment will be described. FIG. 1 is a block diagram that illustrates the entire configuration of the iris authentication system 1 in the present example embodiment.

As illustrated in FIG. 1, the iris authentication system 1 is provided with: a wide camera 2 that is one specific example of a "first imaging apparatus" in the supplementary note described below; a plurality of iris cameras 3 each of which is one specific example of a "second imaging apparatuses" in the supplementary note described below; and an iris authentication apparatus 6 that is one specific example of a "control apparatus" in the supplementary note described below. The iris authentication system 1 is further provided with: a human detection sensor 4 that is one specific example of a "first detection apparatus" in the supplementary note described below; and a human detection sensor 5 that is one specific example of a "second detection apparatus" in the supplementary note described below. FIG. 1 illustrates an example in which the iris authentication system 1 is provided with n (note that n is an integer that is equal to or larger than 2) iris cameras 3. In the below described description, the n iris cameras 3 are referred to as an iris camera 3-1, an iris camera 3-2, ..., and an iris camera 3-$n$, respectively, if needed. Note that the number of the iris cameras 3 may be set appropriately on the basis of a characteristic of each iris camera 3 (for example, at least one of a range of a field of view of each iris camera 3, a resolution of each iris camera 3 and so on)

Figure 2:
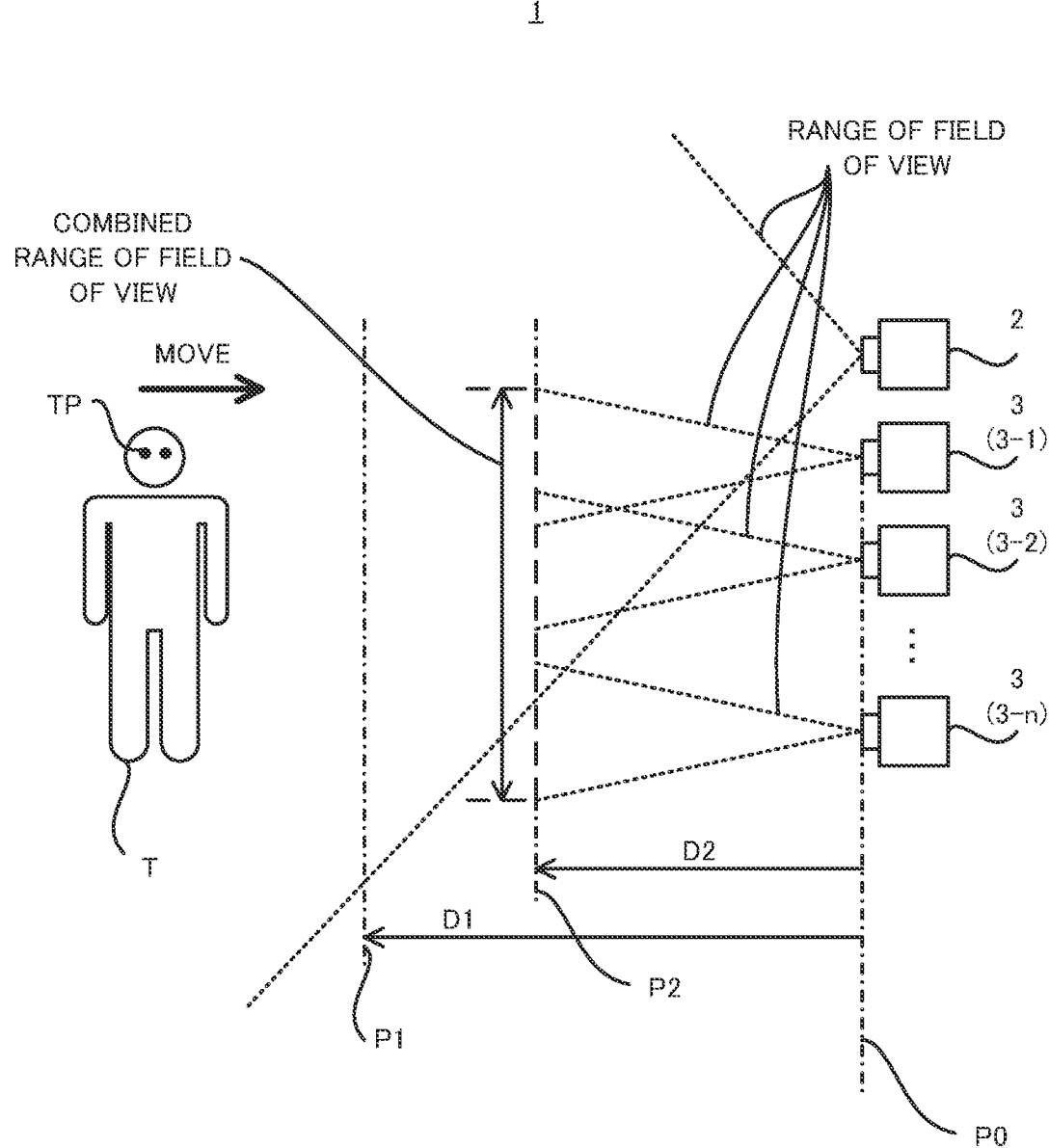
FIG. 2 is a conceptional diagram that illustrates a positional relationship between a wide camera and an iris camera and an authentication target person.

Each of the wide camera 2 and the plurality of iris cameras 3 is an imaging apparatus that is configured to capture an image of the authentication target person T. Next, with reference to FIG. 2, the wide camera 2 and the plurality of iris cameras 3 will be described in more detail. FIG. 2 is a conceptional diagram that illustrates a positional relationship between the wide camera 2 and the plurality of iris cameras 3 and the authentication target person T.

As illustrated in FIG. 2, the wide camera 2 captures the image of the authentication target person T with a range of the field of view that is wider than the range of the field of view of each iris camera 3. Namely, the range of the field of view of the wide camera 2 is wider than the range of the field of view of each iris camera 3. Specifically, the range of the field of view of the wide camera 2 is set to be a proper range so that the wide camera 2 is configured to capture the image of the authentication target person T regardless of the height of the authentication target person T. Namely, the range of the field of view of the wide camera 2 is set to be a proper range so that the wide camera 2 is configured to capture the image of the relatively tall authentication target person T and to capture the image of the relatively short authentication target person T too. Especially, the range of the field of view of the wide camera 2 is set to be a proper range so that the wide camera 2 is configured to capture an image of a target portion TP (an eye including the iris in the present example embodiment) of the authentication target person T that is used for the authentication.

Note that the "range of the field of view of the camera" in the present example embodiment means a range including a scene an image of which is capturable by the camera, and may be referred to as an "imaging range". A size of the range of the field of view typically becomes wider as an angle of view (in other word, a view angle) of the camera becomes wider. Thus, an optical system (for example, a lens) of the wide camera 2 is typically an optical system that has a field of view wider than that of an optical system of each iris camera 3. Namely, an angle of view of the wide camera 2 is wider than an angle of view of each iris camera 3. Moreover, the angle of view of the camera typically becomes wider as a focal length of an optical system (for example, a lens) of the camera becomes shorter. Thus, a focal length of the optical system of the wide camera 2 is shorter than a focal length of the optical system of each iris camera 3.

The wide camera 2 captures the image of the authentication target person T that is located at a trigger point P1. Namely, the range of the field of view of the wide camera 2 is set to be a proper range so that the wide camera 2 is configured to capture the image of the authentication target person T that is located at the trigger point P1. The trigger point P1 is a point that is located on a moving route of the authentication target person T. Moreover, the trigger point P1 is a point that is located at a nearer side than a reference point P0 as seen from the authentication target person T moving toward the trigger point P1. Namely, the trigger point P1 is a point that is located at a backward side (namely, a rear side) than the reference point P0 along a moving direction of the authentication target person T. Moreover, the trigger point P1 is a point that is away from the reference point P0 by a distance D1 along the moving direction of the authentication target person T. The reference point P0 may be a point at which each iris camera 3 is disposed, for example. Alternatively, the reference point P0 may be a destination for the moving authentication target person T, for example. The destination may be a point through which the authentication target person T passes after the authentication (for example, a point at which a gate is disposed in the airport).

In an example illustrated in FIG. 2, the authentication target person T moves from a left side to a right side on a paper. Therefore, in the example illustrated in FIG. 2, the trigger point P1 is a point that is away from the reference point P0 toward the left side on the paper by the distance D1. Note that the authentication target person T may move along a linear route in which the moving direction is always the same, or may move along a route (for example, a curved route or a winding route) in which the driving direction changes in the middle.

It is preferable that the wide camera 2 be disposed so that a focus position of the wide camera 2 is located at the trigger point P1. Incidentally, the "focus position" in the present example embodiment means a certain area that ranges in front and back of a best focus position (for example, an area that is allowed to be regarded as in focus and corresponds to a depth of field). In this case, it is preferable that the wide camera 2 be disposed so that the focus position of the wide camera 2 is an area including the trigger point P1 (namely, so that the trigger point P1 is located in an area corresponding to the focus position). Conversely, the trigger point P1 is set at the focus position of the wide camera 2.

The wide camera 2 has a resolution that allows a face of the authentication target person T located at the trigger point P1 to be recognized from a wide image 200 that is an image captured by the wide camera 2. Especially, the wide camera 2 has a resolution that allows a position in the wide image 200 of the target portion TP (namely, the eye) of the authentication target person T located at the trigger point P1 to be recognized from the wide image 200.

On the other hand, each iris camera 3 captures the image of the authentication target person T that is located at a focus point P2. Namely, the range of the field of view of each iris camera 3 is set to be a proper range so that each iris camera 3 is configured to capture the image of the authentication target person T that is located at the focus point P2. The focus point P2 is a point that is located on the moving route of the authentication target person T, as with the trigger point P1. Moreover, the pint point P2 is a point that is located at a nearer side than the reference point P0 as seen from the authentication target person T moving toward the focus point P2, as with the trigger point P1. Namely, the focus point P2 is a point that is located at a backward side (namely, a rear side) than the reference point P0 along the moving direction of the authentication target person T. Moreover, the focus point P2 is a point that is away from the reference point P0 by a distance D2 along the moving direction of the authentication target person T. In the example illustrated in FIG. 2, the authentication target person T moves from the left side to the right side on the paper. Therefore, in the example illustrated in FIG. 2, the focus point P2 is a point that is away from the reference point P0 toward the left side on the paper by the distance D2.

The distance D2 between the focus point P2 and the reference point P0 is shorter than the distance D1 between the trigger point P1 and the reference point P0. Thus, the focus point P2 is located at a forward side (namely, a front side) than the trigger point P1 along the moving direction of the authentication target person T. In other words, the trigger point P1 is located at a backward side (namely, a rear side) than the focus point P2 along the moving direction of the authentication target person T. Therefore, the moving authentication target person T passes through the focus point P2 after passing through the trigger point P1. In other words, the moving authentication target person T passes through the trigger point P1 before passing through the focus point P2. Note that the distances D1 and D2 may be set to be any values as long as a relationship that the distance D2 is shorter than the distance D1 is satisfied. As one example, the distances D1 and D2 may be set 3m and 2m, respectively.

Each iris camera 3 is disposed so that a focus position of each iris camera 3 is located at the focus point P2. Specifically, it can be said that each iris camera 3 is disposed so that the focus position of each iris camera 3 is an area including the focus point P2 (namely, so that the focus point P2 is located in an area corresponding to the focus position). Conversely, the focus point P2 is set at the focus position of each iris camera 3. Incidentally, since the angle of view of the wide camera 2 is wider than the angle of view of each iris camera 3 (namely, the focal length of the optical system of the wide camera 2 is shorter than the focal length of the optical system of each iris camera 3) as described above, the area corresponding to the focus position of the wide camera 2 is wider than the area corresponding to the focus position of each iris camera 3.

The plurality of iris cameras 3 are disposed so that the ranges of the field of view of the plurality of iris cameras 3 overlap partially in a vertical direction (alternatively, a desired direction that is different from the vertical direction) at the focus point P2. In the example illustrated in FIG. 2, the plurality of iris cameras 3 are disposed so that a lower end part of the range of the field of view of the iris camera 3-$k$ (note that k is an integer that satisfies $1 \leq k \leq n$) and an upper end part of the range of the field of view of the iris camera 3-$m$ (note that m is an integer that satisfies $1 \leq k+1=m \leq n$) overlap at the focus point P2. As a result, scenes that are partially the same are included in two images respectively captured by two iris cameras 2 the range of the field of view of which overlap partially. In the example illustrated in FIG. 2, the same scene is included in a lower end part of the image captured by the iris camera 3-$k$ and an upper end part of the image captured by the iris camera 3-$m$.

The plurality of iris cameras 3 are disposed so that a combined range of field of view that is obtained by combining the ranges of the field of view of the plurality of iris cameras 3 has a predetermined horizontal size in a horizontal direction and has a predetermined vertical size in the vertical direction. The predetermined horizontal size may be a size (for example, 0.2m) that allows the target portion TP of the authentication target person T located at the focus point P2 to be included in the combined range of the field of view. The predetermined vertical size may be a size (for example, 0.4m) that allows the target portion TP of the authentication target person T located at the focus point P2 to be included in the combined range of the field of view regardless of the height of the authentication target person T.

Each iris camera 3 has a resolution that allows the target portion TP of the authentication target person T located at the focus point P2 to be recognized from an iris image 300 that is an image captured by each iris camera 3. Especially, each iris camera 3 has a resolution that allows the pattern of the iris of the authentication target person T located at the focus point P2 to be recognized from the iris image 300 that is the image captured by each iris camera 3.

Note that the range of the field of view of the wide camera 2 partially overlaps with the range of the field of view of at least one of the plurality of iris cameras 3. In this case, both of the authentication target person T (especially, the target portion TP) located at the trigger point P1 and the authentication target person T (especially, the target portion TP) located at the focus point P2 may be included in the range of the field of view of the wide camera 2. For example, both of the authentication target person T (especially, the target portion TP) located at the trigger point P1 and the authentication target person T (especially, the target portion TP) located at the focus point P2 may be included in the range of the field of view of each iris camera 3. However, the range or the field of view of the wide camera 2 may not overlap with the range of the field of view of each of the plurality of iris cameras. For example, the authentication target person T (especially, the target portion TP) located at the trigger point P1 may be included in the range of the field of view of the wide camera 2 and the authentication target person T (especially, the target portion TP) located at the focus point P2 may not be included in the range of the field of view of the wide camera 2. For example, the authentication target person T (especially, the target portion TP) located at the focus point P2 may be included in the range of the field of view of each iris camera 3 and the authentication target person T (especially, the target portion TP) located at the trigger point P1 may not be included in the range of the field of view of each iris camera 3.

Again in FIG. 1, the human detection sensor 4 is a detection apparatus for detecting whether or not the authentication target person T is located at the trigger point P1. A detected result by the human detection sensor 4 is outputted to the iris authentication apparatus 6. The detected result by the human detection sensor 4 is used as a condition to determine whether or not the wide camera 2 captures the image of the authentication target person T located at the trigger point P1.

The human detection sensor 5 is a detection apparatus for detecting whether or not the authentication target person T is located at the focus point P2. A detected result by the human detection sensor 5 is outputted to the iris authentication apparatus 6. The detected result by the human detection sensor 5 is used as a condition to determine whether or not the iris camera 3 captures the image of the authentication target person T located at the focus point P2.

The iris authentication apparatus 6 controls an entire operation of the iris authentication system 1. Especially in the present example embodiment, the iris authentication apparatus 6 performs an iris authentication operation. The iris authentication operation is an operation that includes a process of selecting one iris camera 3 for capturing the image of the authentication target person T located at the focus point P2 from the plurality of iris cameras 3 on the basis of the wide image 200 captured by the wide camera 2 and a process of performing the authentication of the authentication target person T on the basis of the iris image 300 captured by the selected one iris camera 3, for example.

(1-2) Configuration of Iris Authentication Apparatus 6

Figure 3:
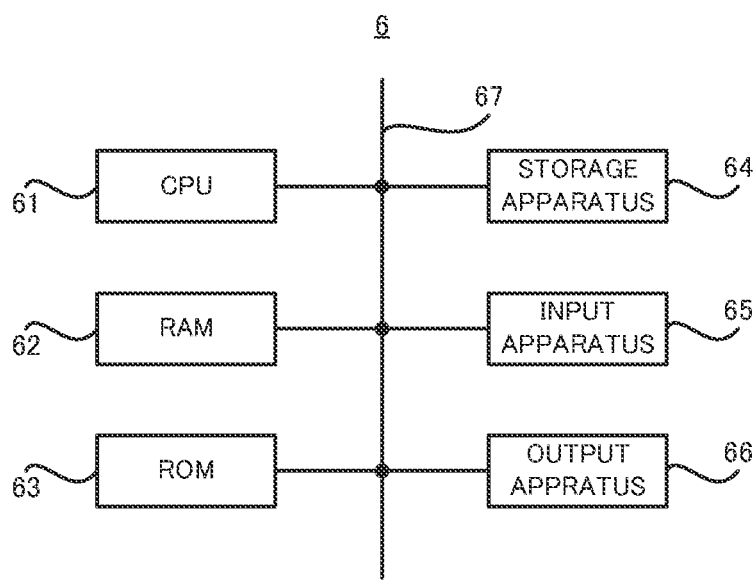
FIG. 3 is a block diagram that illustrates a hardware configuration of an iris authentication apparatus in the present example embodiment.

Next, with reference to FIG. 3, a configuration of the iris authentication apparatus 6 will be described. FIG. 3 is a block diagram that illustrates a hardware configuration of the iris authentication apparatus 6 in the present example embodiment.

As illustrated in FIG. 3, the iris authentication apparatus 6 is provided with a CPU (Central Processing Unit) 61, a RAM (Random Access Memory) 62, a ROM (Read Only Memory) 63, a storage apparatus 64, an input apparatus 65, and an output apparatus 66. The CPU 61, the RAM 62, the ROM 63, the storage apparatus 64, the input apparatus 65, and the output apparatus 66 are interconnected through a data bus 67. However, the iris authentication apparatus 6 may not be provided with at least one of the RAM 62, the ROM 63, the storage apparatus 64, the input apparatus 65, and the output apparatus 66.

The CPU 61 reads a computer program. For example, the CPU 61 may read a computer program stored in at least one of the RAM 62, the ROM 63 and the storage apparatus 64. For example, the CPU 61 may read a computer program stored in a computer-readable recording medium, by using a not-illustrated recording medium reading apparatus. The CPU 61 may obtain (namely, read) a computer program from a not-illustrated apparatus disposed outside the iris authentication apparatus 6, through a network interface. The CPU 61 controls the RAM 62, the storage apparatus 64, the input apparatus 65, and the output apparatus 66 by executing the read computer program. Especially in the present example embodiment, when the CPU 61 executes the read computer program, a logical functional block(s) for performing the iris authentication operation is implemented in the CPU 61. Namely, the CPU 61 is configured to function as a controller for implementing the logical block for performing the iris authentication operation.

Figure 4:
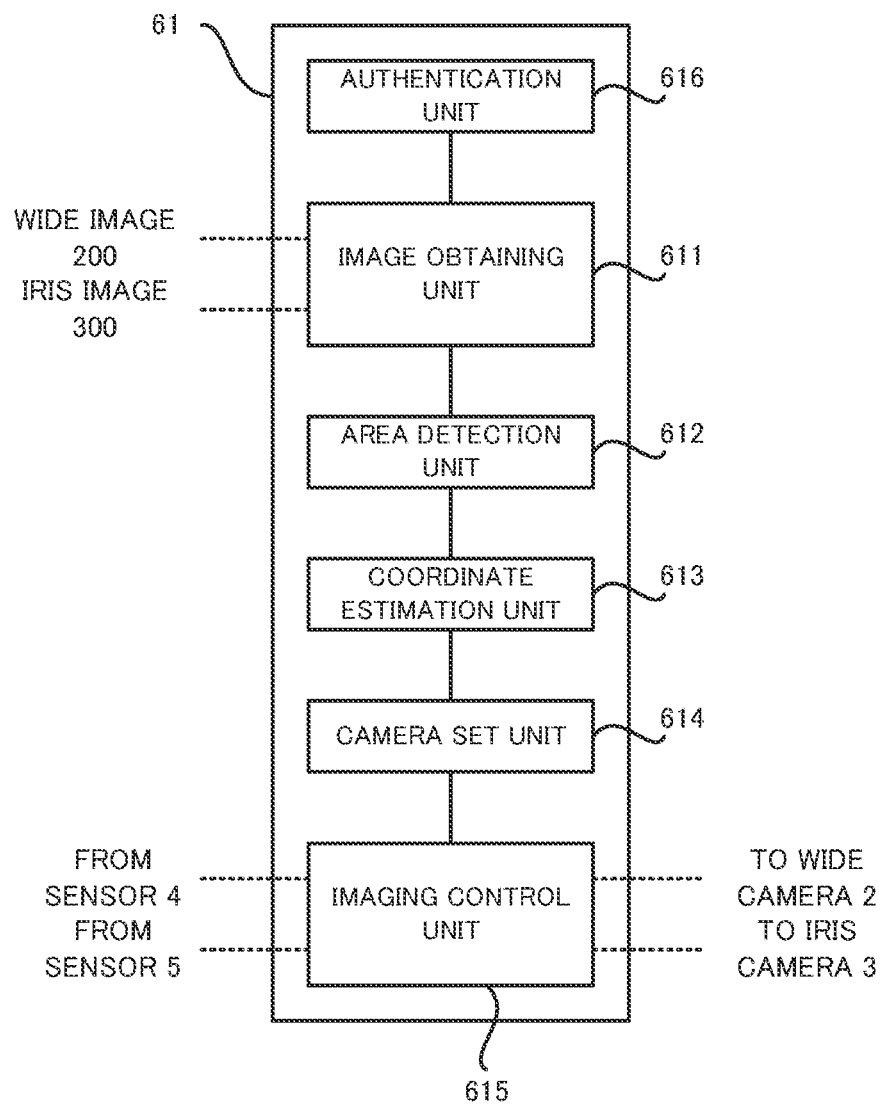
FIG. 4 is a block diagram that illustrates a functional block implemented in a CPU of the iris authentication apparatus in the present example embodiment.

One example of the logical block that is implemented in the CPU 61 for performing the iris authentication operation is illustrated in FIG. 4. As illustrated in FIG. 4, in the CPU 61, an image obtaining unit 611 that is one specific example of a "obtaining unit" in the supplementary note described below, an area detection unit 612 that is one specific example of a "controlling unit" in the supplementary note described below, a coordinate estimation unit 613 that is one specific example of the "controlling unit" in the supplementary note described below, a camera set unit 614 that is one specific example of the "controlling unit" in the supplementary note described below, an imaging control unit 615 that is one specific example of the "controlling unit" in the supplementary note described below, and an authentication unit 616 are implemented as logical blocks for performing the iris authentication operation. Note that an operation of each of the image obtaining unit 611, the area detection unit 612, the coordinate estimation unit 613, the camera set unit 614, the imaging control unit 615 and the authentication unit 616 will be described later in detail with reference to FIG. 5, and thus, the detailed description thereof is omitted here.

Again in FIG. 3, The RAM 62 temporarily stores the computer program to be executed by the CPU 61. The RAM 62 temporarily stores the data that is temporarily used by the CPU 61 when the CPU 61 executes the computer program. The RAM 62 may be, for example, a D-RAM (Dynamic RAM).

The ROM 63 stores the computer program to be executed by the CPU 61. The ROM 63 may otherwise store fixed data. The ROM 63 may be, for example, a P-ROM (Programmable ROM).

The storage apparatus 64 stores the data that is stored for a long term by the iris authentication apparatus 6. The storage apparatus 64 may operate as a temporary storage apparatus of the CPU 61. The storage apparatus 64 may include, for example, at least one of a hard disk apparatus, a magneto-optical disk apparatus, an SSD (Solid State Drive), and a disk array apparatus.

The input apparatus 65 is an apparatus that receives an input instruction from a user of the iris authentication apparatus 6. The input apparatus 65 may include, for example, at least one of a keyboard, a mouse, and a touch panel.

The output apparatus 66 is an apparatus that outputs an information about the iris authentication apparatus 6, to the outside. For example, the output apparatus 66 may be a display apparatus that is configured to display an information about the iris authentication apparatus 6.

(2) FLOW OF IRIS AUTHENTICATION OPERATION

Figure 5:
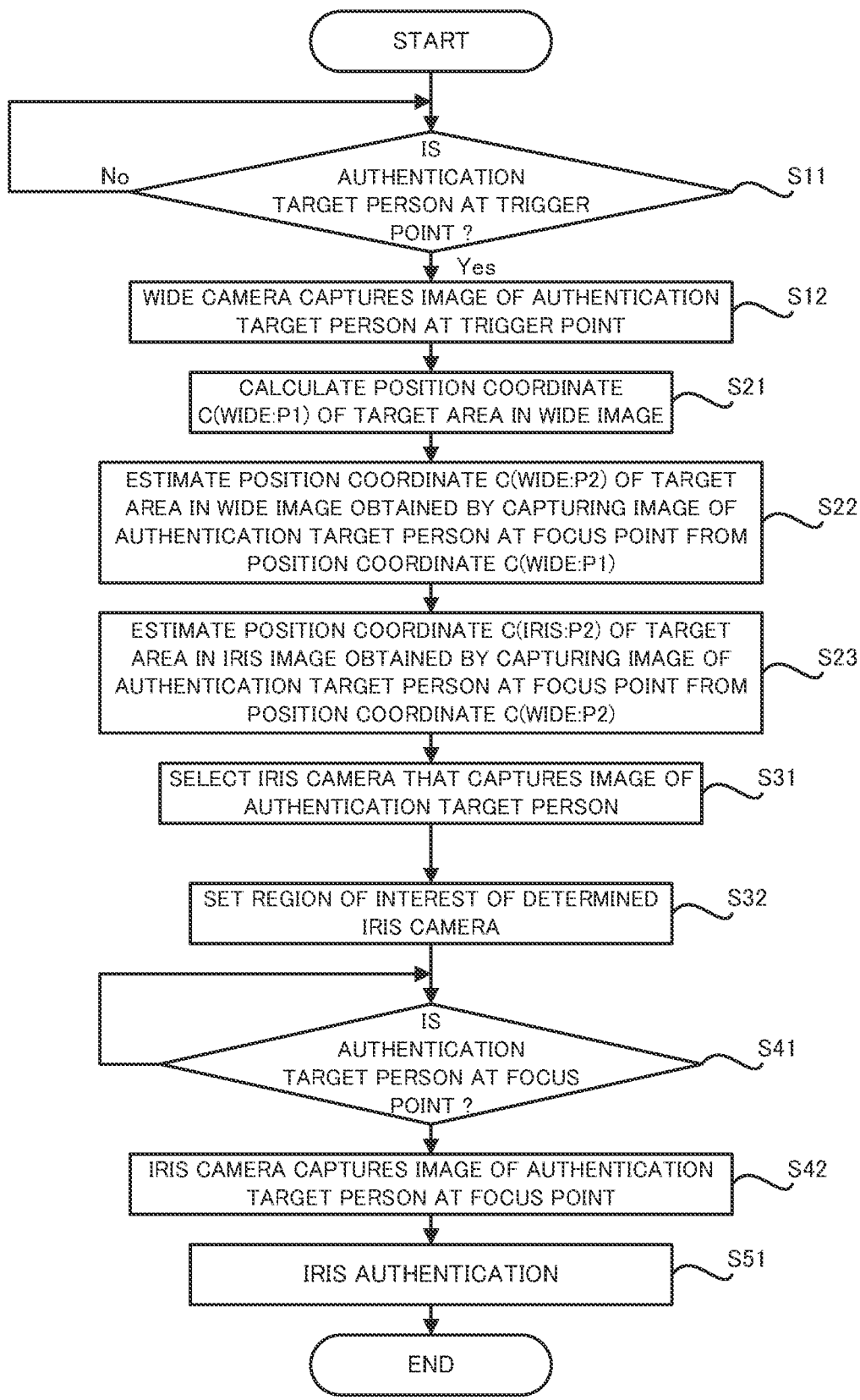
FIG. 5 is a flow chart that illustrates a flow of an operation of the iris authentication system (namely, an iris authentication operation) in the present example embodiment.

Next, with reference to FIG. 5, a flow of the operation (namely, the iris authentication operation) of the iris authentication system 1 in the present example embodiment will be described. FIG. 5 is a flow chart that illustrates the flow of the operation (namely, the iris authentication operation) of the iris authentication system 1 in the present example embodiment.

As illustrated in FIG. 5, the imaging control unit 615 determines whether or not the authentication target person T is located at the trigger point P1 on the basis of the detected result by the human detection sensor 4 (a step S11). As a result of the determination at the step S11, when it is determined that the authentication target person T is not located at the trigger point P1 (the step S11: No), the process at the step S11 is repeatedly performed. On the other hand, as a result of the determination at the step S11, when it is determined that the authentication target person T is located at the trigger point P1 (the step S11: Yes), the imaging control unit 615 controls the wide camera 2 to capture the image of the authentication target person T located at the trigger point P1 (a step S12). As a result, the wide camera 2 captures the image of the authentication target person T located at the trigger point P1 (the step S12). The wide image 200 captured by the wide camera 2 is obtained by the image obtaining unit 611 (the step S12).

Figure 6:
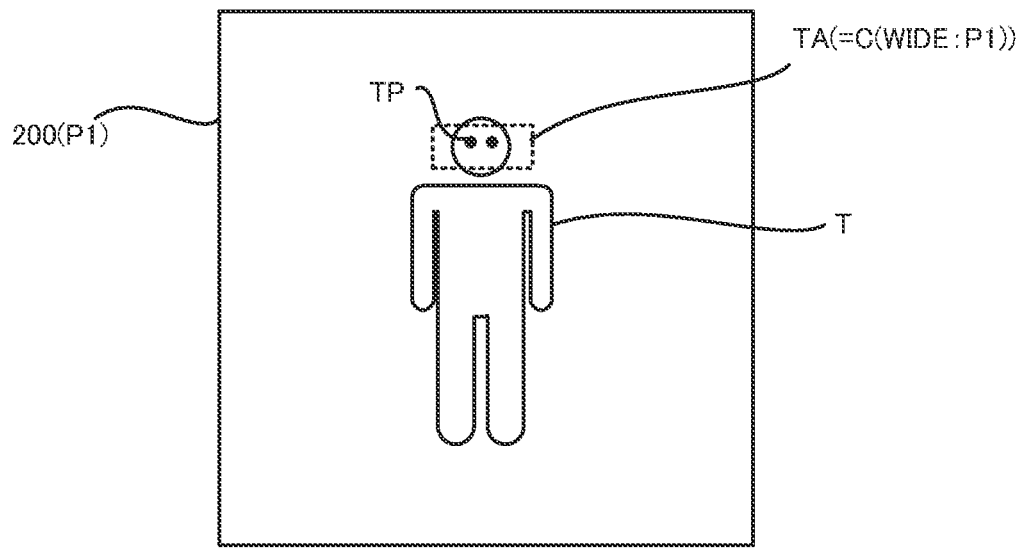
FIG. 6 is a planar view that illustrates one example of a wide image.

Then, the area detection unit 612 detects, as a target area TA, an image part of the wide image 200 in which the target portion TP is included by performing an image processing on the wide image 200 obtained at the step S12 (a step S21). For example, as illustrated in FIG. 6 that is a planar view illustrating one example of the target area TA in the wide image 200, the area detection unit 612 detects, as the target area TA, a rectangular (alternatively, another shaped) image part of the wide image 200 in which the target portion TP is included. Furthermore, the area detection unit 612 calculates a position coordinate C of the detected target area TA in the wide image 200 (the step S21). The position coordinate C may include a coordinate of a desired part (for example, a corner part) of the target area TA. The position coordinate C is typically a two-dimensional coordinate (alternatively, a two-dimensional vector). Note that the position coordinate C that is calculated at the step S21 is referred to as a "position coordinate C(wide:P1)" in the below described description for convenience of description.

Then, the coordinate estimation unit 613 estimates, on the basis of the position coordinate C(wide:P1) of the target area TA that is calculated at the step S21, the position coordinate C of the target area TA in the wide image 200 that is obtained under the assumption that the wide camera 2 has captured the image of the authentication target person T that is located at the focus point P2 (a step S22). More specifically, the coordinate estimation unit 613 estimates the position coordinate C of the target area TA in the wide image 200 that is expected to be obtained under the assumption that the wide camera 2 has captured the image of the authentication target person T that has moved from the trigger point P1 to the focus point P2 (the step S22). Namely, the coordinate estimation unit 613 estimates the position coordinate C of the target area TA in the wide image 200 that is expected to be obtained under the assumption that the wide camera 2 has captured the image of the authentication target person T that is located at the focus point P2 in a situation where the authentication target person T located at the trigger point P1 has moved to the focus point P2 (the step S22). Note that the position coordinate C that is estimated at the step S22 is referred to as a "position coordinate C(wide:P2)" in the below described description for convenience of description. Moreover, in the below described description, the wide image 200 that is actually obtained by means of the wide camera 2 capturing the image of the authentication target person T located at the trigger point P1 is referred to as a "wide image 200(P1)" and the wide image 200 that is expected to be obtained under the assumption that the wide camera 2 has captured the image of the authentication target person T that has moved from the trigger point P1 to the focus point P2 is referred to as a "wide image 200(P2)" to distinguish the both, for convenience of description.

Figure 7:
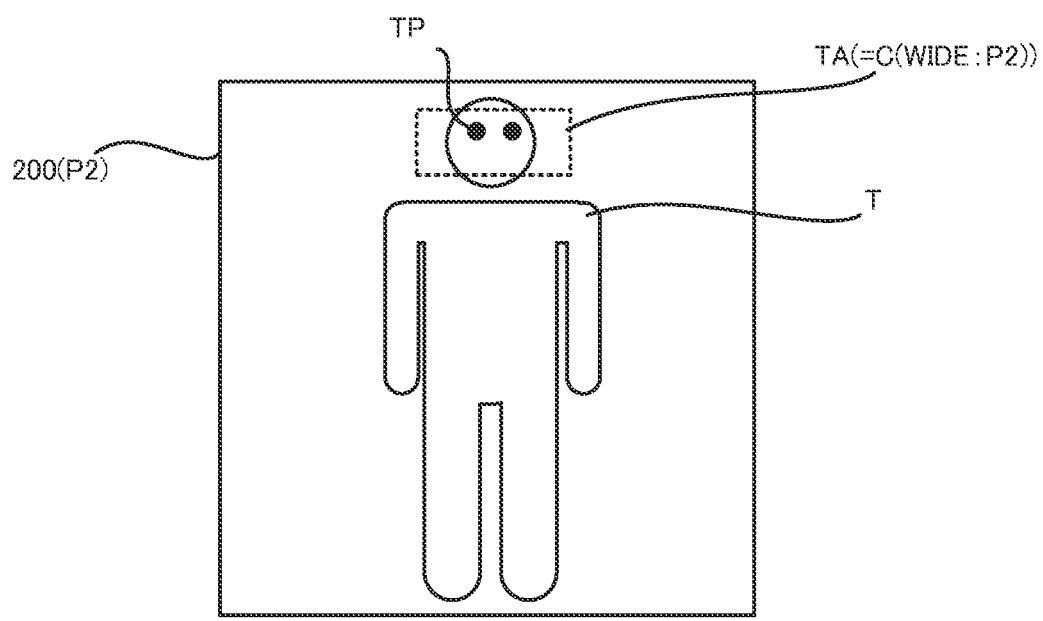
FIG. 7 is a planar view that illustrates one example of the wide image.

Since the trigger point P1 is different from the focus point P2, there is a high possibility that at least one of a size and a position of the authentication target person T in the wide image 200(P1) is different from at least one of a size and a position of the authentication target person T in the wide image 200(P2), as illustrated in FIG. 6 that illustrates the wide image 200(P1) and FIG. 7 that illustrates the wide image 200(P2). Especially, there is a high possibility that at least one of the size and the position of the authentication target person T in the wide image 200(P1) is even more different from at least one of the size and the position of the authentication target person T in the wide image 200(P2), as the trigger point P1 is away from the focus point P2 more. Thus, there is typically a high possibility that the position coordinate C(wide:P1) is different from the position coordinate C(wide:P2).

The coordinate estimation unit 613 may estimate the position coordinate C(wide:P2) from the position coordinate C(wide:P1) by using a first correspondence information that indicates a correspondence (typically, a positional relationship) between an object included in the wide image 200(P1) and the same object included in the wide image 200(P2). This first correspondence information typically indicates a correspondence between a position coordinate in the wide image 200(P1) of the object included in the wide image 200(P1) and a position coordinate in the wide image 200(P2) of the same object included in the wide image 200(P2) that is expected to be obtained when the object has moved from the trigger point P1 to the focus point P2 as with the authentication target person T. Thus, the first correspondence information is substantially information to which a moving aspect of the authentication target person T (for example, a moving direction of the authentication target person T) is reflected. Namely, the first correspondence information substantially information relating to the moving aspect of the authentication target person T (for example, the moving direction of the authentication target person T).

The first correspondence information may be calculated in advance (for example, before the iris authentication operation is performed) on the basis of the wide image 200 that is obtained by means of the wide camera 2 actually capturing the image of the object located at the trigger point P1 and the wide image 200 that is obtained by means of the wide camera 2 actually capturing the image of the same object that has moved from the trigger point P1 to the focus point P2 as with the authentication target person T. Specifically, the first correspondence information may be calculated on the basis of the position coordinate in the wide range 200 of the object located at the trigger point P1 and the position coordinate in the wide range 200 of the object located at the focus point P2. Alternatively, the wide image 200 that is expected to be obtained when the wide camera 2 captures the image of the object located at the trigger point P1 and the wide image 200 that is expected to be obtained when the wide camera 2 captures the image of the object that has moved from the trigger point P1 to the focus point P2 as with the authentication target person T may be calculated by a simulation and the like, and the first correspondence information may be calculated on the basis of a result of the simulation in advance. In the simulation, at least one of a position of the wide camera 2, a camera parameter of the wide camera 2, a position of the trigger point P1 and a position of the focus point P2 may be considered. Alternatively, the first correspondence information may be calculated by any other method.

A first transformation matrix H1 that transforms the position coordinate C(wide:P1) to the position coordinate C(wide:P2) is one example of the first correspondence information. In this case, the coordinate estimation unit 613 may estimate the position coordinate C(wide:P2) by using an equation of position coordinate C(wide:P2)=H1×position coordinate C(wide:P1). This first transformation matrix H1 may be a matrix that represents a projective transformation to project an object located at the trigger point P1 onto a virtual plane located at the focus point P2, for example.

Then, the coordinate estimation unit 613 estimates, on the basis of the position coordinate C(wide:P2) that is estimated at the step S22, the position coordinates C of the target areas TA in the plurality of iris images 300 that are obtained, respectively, under the assumption that the plurality of iris cameras 3 have captured the image of the authentication target person T that is located at the focus point P2 (a step S23). More specifically, the coordinate estimation unit 613 estimates the position coordinates C of the target areas TA in the plurality of iris images 300 that are expected to be obtained, respectively, under the assumption that the plurality of iris cameras 3 have captured the image of the authentication target person T that has moved from the trigger point P1 to the focus point P2 (the step S23). Namely, the coordinate estimation unit 613 estimates the position coordinates C of the target areas TA in the plurality of iris images 300 that are expected to be obtained, respectively, under the assumption that the plurality of iris cameras 3 have captured the image of the authentication target person T that is located at the focus point P2 in a situation where the authentication target person T located at the trigger point P1 has moved to the focus point P2 (the step S23). Note that the position coordinate C that is estimated at the step S23 is referred to as a "position coordinate C(iris:P2)" in the below described description for convenience of description. Moreover, in the below described description, the iris image 300 that is expected to be obtained under the assumption that each iris camera 3 has captured the image of the authentication target person T that has moved from the trigger point P1 to the focus point P2 is referred to as an "iris image 300(P2)".

Figure 8:
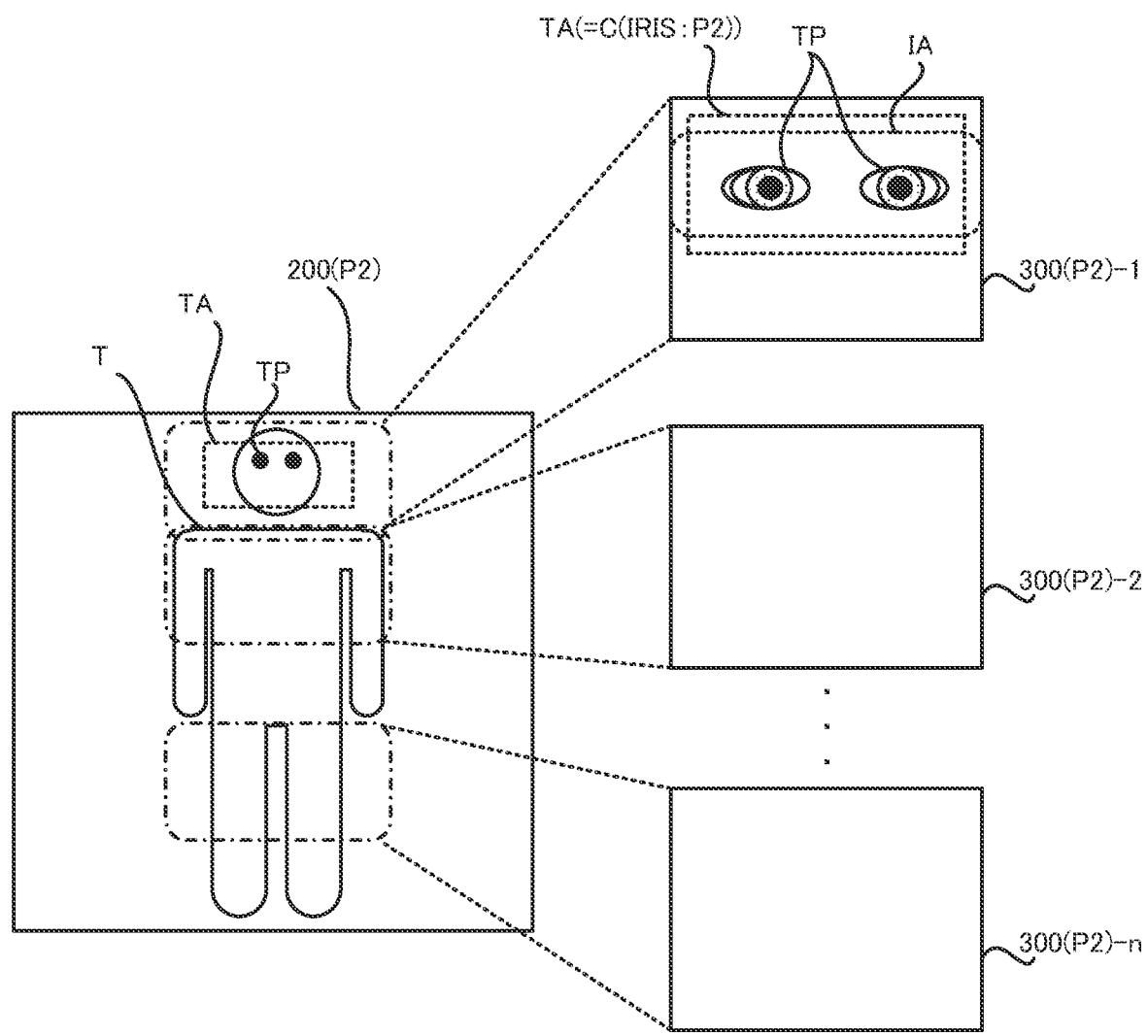
FIG. 8 is a planar view that illustrates a relationship between the wide image and a plurality of iris images.

As described above, the range of the field of view of each iris camera 3 is narrower than the range of the field of view of wide camera 2. Thus, as illustrated in FIG. 8 that illustrates a relationship between the wide image 200(P2) and the plurality of iris images 300, the target area TA included in the wide image 200(P2) is not necessarily included in all of the plurality of iris images 300(P2). Namely, there is a possibility that the plurality of iris images 300(P2) include both of the iris image 300(P2) in which the target area TA is included and the iris image 300(P2) in which the target area TA is not included. In an example illustrated in FIG. 8, the target area TA is included in the iris image 300(P2)-1 that is expected to be captured by the iris camera 3-1 and is not included in the iris images 300(P2)-2 to 300(P2)-n that are expected to be captured by the iris cameras 3-2 to 3-n. Thus, at the step S23, the coordinate estimation unit 613 determines, on the basis of the position coordinate C(wide:P2), the iris image 300(P2) in which the target area TA is expected to be included, and estimates the position coordinate C(iris:P2) of the target area TA in the determined iris image 300(P2).

The coordinate estimation unit 613 may estimate the position coordinate C(iris:P2) from the position coordinate C(wide:P2) by using a second correspondence information that indicates a correspondence (typically, a positional relationship) between an object included in the wide image 200(P2) and the same object included in each of the plurality of iris images 300(P2). This second correspondence information typically indicates a correspondence between a position coordinate in the wide image 200(P2) of the object included in the wide image 200(P2) and a position coordinate in the iris image 300(P2) of the same object included in each of the plurality of iris images 300(P2).

The second correspondence information may be calculated in advance (namely, before the iris authentication operation is performed) on the basis of the wide image 200 that is obtained by means of the wide camera 2 actually capturing the image of the object located at the focus point P2 and the plurality of iris images 300 that are obtained by means of the plurality of iris cameras 3 actually capturing the image of the same object that is located at the focus point P2, respectively. Specifically, the second correspondence information may be calculated on the basis of the position coordinate in the wide range 200 of the object at the focus point P2 and the position coordinate in the iris range 300 of the object at the focus point P2. Alternatively, the wide image 200 that is expected to be obtained when the wide camera 2 captures the image of the object located at the focus point P2 and the plurality of iris images 300 that are expected to be obtained when the plurality of iris cameras 3 capture the image of the same object that is located at the focus point P2, respectively, may be calculated by a simulation and the like, and the second correspondence information may be calculated on the basis of a result of the simulation in advance. In the simulation, at least one of the position of the wide camera 2, the camera parameter of the wide camera 2, positions of the plurality of iris cameras 3, camera parameters of the plurality of iris cameras 3, the position of the trigger point P1 and the position of the focus point P2 may be considered. Alternatively, the second correspondence information may be calculated by any other method.

A second transformation matrix H2 that transforms the position coordinate C(wide:P2) to the position coordinate C(iris:P2) is one example of the second correspondence information. In this case, the coordinate estimation unit 613 may estimate the position coordinate C(iris:P2) by using an equation of position coordinate C(iris:P2)=H2×position coordinate C(wide:P2).

Then, the camera set unit 614 selects, on the basis of the position coordinate C(iris:P2) that is estimated at the step S23, one iris camera 3 for capturing the image of the authentication target person T located at the focus point P2 from the plurality of iris cameras 3 (a step S31). Specifically, as described above, the coordinate estimation unit 613 determines, on the basis of the position coordinate C(wide: P2), the iris image 300(P2) in which the target area TA is included. Therefore, the camera set unit 614 selects, as one iris camera 3 for capturing the image of the authentication target person T located at the focus point P2, the iris camera 3 of the plurality of iris cameras 3 that corresponds to the iris image 300(P2) in which the target area TA is included. In the example illustrated in FIG. 8, the camera set unit 614 selects the iris camera 3-1 that corresponds to the iris image 300(P2)-1 as one iris camera 3 for capturing the image of the authentication target person T located at the focus point P2.

Then, the camera set unit 614 sets a region of interest (ROI: Region of Interest) IA that defines an image part, which is actually obtained (namely, read) for performing the iris authentication, of the iris image 300 captured by one iris camera 3 selected at the step S31 (a step S32). Specifically, as illustrated in FIG. 8, the camera set unit 614 sets, to the region of interest IA, a rectangular (alternatively, another shaped) area, in which the target portion TP is expected to be included, of the iris image 300 captured by selected one iris camera 3. Namely, as illustrated in FIG. 8, the camera set unit 614 sets, to the region of interest IA, a rectangular (alternatively, another shaped) area, which includes the target area TA, corresponds to the target area TA or is expected to be included in the target area TA, of the iris image 300 captured by selected one iris camera 3, for example. As described above, the position coordinate C(iris: P2) estimated at the step S23 indicates the position coordinate of the target area TA in the iris image 300(P2). Since the target portion TP is included in the target area TA, the camera set unit 614 is able to set the region of interest IA properly on the basis of the position coordinate C(iris:P2). In the example illustrated in FIG. 8, the camera set unit 614 sets a part of the iris image 300(P2)-1 to the region of interest IA.

When the region of interest IA is set, the iris authentication system 1 operates in a region of interest mode. In this case, the image obtaining unit 611 obtains an image part of the iris image 300 (namely, a part of an image data of the iris image 300) in the region of interest IA, instead of obtaining whole of the iris image 300 captured by the iris camera 3. Namely, the image obtaining unit 611 may not obtain an image part of the iris image 300 (namely, a residual part of the image data of the iris image 300) in an area other than the region of interest IA. As a result, a frame rate at which the image obtaining unit 611 obtains the iris image 300 from the iris camera 3 substantially improves, compared to a case where whole of the iris image 300 is obtained. For example, when a half area of the iris image 300 is set to the region of interest IA, the frame rate improves to be the double, compared to a case where whole of the iris image 300 is obtained. Thus, even when the frame rate of the iris camera 3 itself is lower than a frame rate that is necessary for the iris authentication, the image obtaining unit 611 is able to obtain the iris image at the frame rate that is necessary for the iris authentication.

Then, the imaging control unit 615 determines whether or not the authentication target person T is located at the focus point P2 on the basis of the detected result by the human detection sensor 5 (a step S41). Namely, the imaging control unit 615 determines whether or not the authentication target person T that has been determined to be located at the trigger point P1 moves to the focus point P2 on the basis of the detected result by the human detection sensor 5 (the step S41). As a result of the determination at the step S41, when it is determined that the authentication target person T is not located at the focus point P2 (the step S41: No), the process at the step S41 is repeatedly performed. On the other hand, as a result of the determination at the step S41, when it is determined that the authentication target person T is located at the focus point P2 (the step S41: Yes), the imaging control unit 615 controls one iris camera 3 selected at the step S31 to capture the image of the authentication target person T located at the focus point P2 (a step S42). As a result, the selected one iris camera 3 captures the image of the authentication target person T located at the focus point P2 (the step S42). The iris image 300 captured by the selected one iris camera 3 (especially, the image part of the iris image 300 in the region of interest IA) is obtained by the image obtaining unit 611 (the step S42).

Then, the authentication unit 616 performs the iris authentication by using the iris image 300 obtained at the step S42 (a step S51). For example, the authentication unit 616 determines the patter of the iris of the authentication target person T on the basis of the iris image 300 obtained at the step S42. Then, the authentication unit 616 determines whether or not the determined pattern matches a pattern that is registered in a data base stored in the storage apparatus 64 and the like. When the determined pattern matches the pattern registered in the database, the authentication unit 616 determines that the authentication target person T is a proper person. When the determined pattern matches the pattern registered in the database, the authentication unit 616 determines that the authentication target person T is not a proper person.

(3) TECHNICAL EFFECT OF IRIS AUTHENTICATION SYSTEM 1

As described above, in the iris authentication system 1, the wide camera 2 captures the image of the authentication target person T that is located at the trigger point P1 that is different from (specifically, is located at a backward side of) the focus point P2 before the iris camera 3 captures the image of the authentication target person T that is located at the focus point P2. Thus, the iris authentication system 1 is able to select one iris camera 3 for capturing the image of the authentication target person T before the authentication target person T is located at the focus point P2. In other words, the iris authentication system 1 is able to select one iris camera 3 for capturing the image of the authentication target person T (furthermore, setting the region of interest IA) by using a time during which the authentication target person T moves from the trigger point P1 to the focus point P2. Thus, the iris authentication system 1 is able to capture the image of the moving authentication target person T (especially, the target portion TP thereof) properly.

Even when the trigger point P1 is different from the focus point P2 as described above, the iris authentication system 1 is able to select one iris camera 3 for capturing the image of the authentication target person T properly on the basis of the wide image 200(P1) captured by the wide camera 2. This is because the iris authentication system 1 estimates, on the basis of the position coordinate C(wide:P1) of the target area TA in the wide image 200(P2), the position coordinate C(wide:P2) of the target area TA in the wide image 200(P2) that is expected to be obtained under the assumption that the wide camera 2 has captured the image of the authentication target person T that has moved to the focus point P2, and then, estimates the position coordinate C(iris:P2) of the target area TA in the iris image 300(P2) that is expected to be obtained under the assumption that the iris camera 3 has captured the image of the authentication target person T that has moved to the focus point P2

Here, since the trigger point P1 is different from the focus point P2, there is a high possibility that the position coordinate C(wide:P1) is different from the position coordinate C(wide:P2) as described above, as illustrated in FIG. 6 and FIG. 7 described above. Therefore, if the position coordinate C(wide:P1) is used as the position coordinate C(wide:P2) as it is, one iris camera 3 that is selected to capture the image of the authentication target person T is not able to capture the image of the target portion TP properly. Namely, if the position coordinate C(wide:P1) is used as the position coordinate C(wide:P2) as it is, there is a possibility that the camera set unit 614 mistakenly selects, as one iris camera 3 for capturing the image of the authentication target person T, the iris camera 3 that is not able to capture the image of the target portion TP of the authentication target person T located at the focus point P2. However, in the present example embodiment, the position coordinate C(wide:P2) is estimated from the position coordinate C(wide:P1) and then the position coordinate C(iris:P2) is estimated. Thus, there is lower possibility that one iris camera 3 that is selected to capture the image of the authentication target person T is not able to capture the image of the target portion TP properly. Namely, there is a lower possibility that the iris camera 3 that is not able to capture the image of the target portion TP of the authentication target person T located at the focus point P2 is mistakenly selected as one iris camera 3 for capturing the image of the authentication target person T. Thus, it can be said that a process of estimating the position coordinate C(wide:P2) from the position coordinate C(wide:P1) contributes a proper selection of the iris camera 3 that captures the image of the target portion TP of the authentication target person T located at the focus point P2 (namely, a proper imaging of the target portion TP by the iris camera 3).

Moreover, in the present example embodiment, the plurality of human detection sensors (namely, the human detection sensors 4 and 5) that correspond to the trigger point P1 and the focus point P2, respectively, are disposed. Thus, the iris authentication system 1 is able to properly determine whether or not the authentication target person T is located at each of the trigger point P1 and the focus point P2. Namely, the iris authentication system 1 is able to properly capture the image of the authentication target person T that is located at the trigger point P1 by the wide camera 2 and is able to properly capture the image of the authentication target person T that is located at the focus point P2 by the iris camera 3.

(4) MODIFIED EXAMPLE

(4-1) First Modified Example

Figure 9:
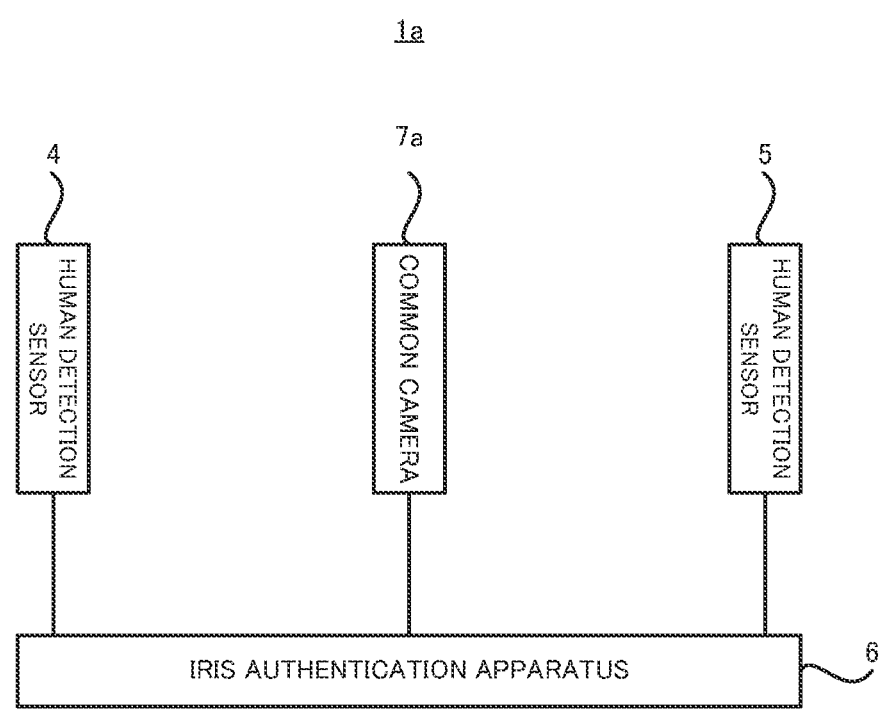
FIG. 9 is a block diagram that illustrates an entire configuration of an iris authentication system in a first modified example.

(4-1-1) Configuration of Iris Authentication System a in First Modified Example Firstly, with reference to FIG. 9, an entire configuration of an iris authentication system 1a in a first modified example will be described. FIG. 9 is a block diagram that illustrates the entire configuration of the iris authentication system 1a in the first modified example. Note that a detailed description of a component that is same as a component of the above described iris authentication system 1 is omitted by assigning the same reference number thereto.

As illustrated in FIG. 9, the iris authentication system 1a is different from the iris authentication system 1 in that it is provided with a single common camera 7a instead of the wide camera 2 and the plurality of iris cameras 3. Another characteristic of the iris authentication system 1a may be same as another characteristic of iris authentication system 1.

The common camera 7a is an imaging apparatus that is configured to capture the image of the authentication target person T, as with the wide camera 2 and the plurality of iris cameras 3. The common camera 7a is configured to switch a state thereof between a wide imaging state in which it is configured to serve as the wide camera 2 and an iris imaging state in which it is configured to serve as at least one of the plurality of iris cameras 3. Note that the wide imaging state and the iris imaging state are examples of a "first state" and a "second state" in the supplementary note described below, respectively.

The common camera 7a in the wide imaging state is equivalent to the above described wide camera 2. Namely, the common camera 7a in the wide imaging state operates as with the above described wide camera 2. Thus, a characteristic of the common camera 7a in the wide imaging state may be same as the above described wide camera 2, and thus, its detailed description is omitted.

The common camera 7a in the iris imaging state is equivalent to at least one of the plurality of iris cameras 3 described above. Namely, the common camera 7a in the iris imaging state operates as with at least one of the plurality of iris cameras 3 described above. Thus, a characteristic of the common camera 7a in the iris imaging state may be same as at least one of the plurality of iris cameras 3 described above, and thus, its detailed description is omitted. Note that the range of the field of view of the common camera 7a in the iris imaging state is typically same as the combined range of the field of view (see FIG. 2) that is obtained by combining the ranges of the field of view of the plurality of iris cameras 3. Thus, the common camera 7a in the iris imaging state is substantially equivalent to the plurality of iris cameras 3 described above that is regarded as a single camera.

In order to switch the state, the common camera 7a may be provided with an optical system having a variable optical characteristic (for example, a focal length), for example. In this case, the focal length of the common camera 7a in the wide imaging state is typically shorter than the focal length of the common camera 7a in the iris imaging state. As a result, the common camera 7a is configured to serve as the wide camera 2 and is configured to serve as at least one of the plurality of iris cameras 3.

As one example, the common camera 7a may be provided with an optical system including what we call a zoom lens. In this case, when a focal length of the optical system including the zoom lens is set to be a relatively short first distance (for example, a first distance that corresponds to the focal length of the above described wide camera 2), the state of the common camera 7a is the wide imaging state. Namely, a focus position of the common camera 7a is set at the area including the trigger point P1 and the common camera 7a is configured to capture the image of the authentication target person T located at the trigger point P1 with the relatively wide range of the field of view (namely, with the relatively wide angle of view). On the other hand, when the focal length of the optical system including the zoom lens is set to be a relatively long second distance (for example, a second distance that corresponds to the focal length of the above described iris camera 3) from the first distance, the state of the common camera 7a is switched from the wide imaging state to the iris imaging state. Namely, the focus position of the common camera 7a is set at the area including the focus point P2 and the common camera 7a is configured to capture the image of the authentication target person T located at the focus point P2 with the relatively narrow range of the field of view (namely, with the relatively narrow angle of view). Moreover, when the focal length of the optical system including the zoom lens is set to be the first distance from the second distance, the state of the common camera 7a is switched from the iris imaging state to the wide imaging state.

In the first modified example, an operation including a process of setting, on the basis of the image captured by the common camera 7a in the wide imaging state, the region of interest (ROI. Region of Interest) IA that defines the image part, which is actually obtained (namely, read) for performing the iris authentication, of the image captured by the common camera 7a in the iris imaging state and a process of performing the authentication of the authentication target person T on the basis of the image captured by the common camera 7a in the iris imaging state, is performed as the iris authentication operation, for example. Next, the iris authentication operation in the first modified example will be described in more detail. Incidentally, in the below described description, the image captured by the common camera 7a in the wide imaging state is referred to as the "wide image 200" for convenience of description, because the image captured by the common camera 7a in the wide imaging state is substantially equivalent to the wide image 200 captured by the wide camera 2. Moreover, the image captured by the common camera 7a in the iris imaging state is referred to as the "iris image 300" for convenience of description, because the image captured by the common camera 7a in the iris imaging state is substantially equivalent to an image that is obtained by combining the plurality of iris images 300 captured by the plurality of iris cameras 3, respectively.

(4-1-2) Flow of Iris Authentication Operation in First Modified Example

Figure 10:
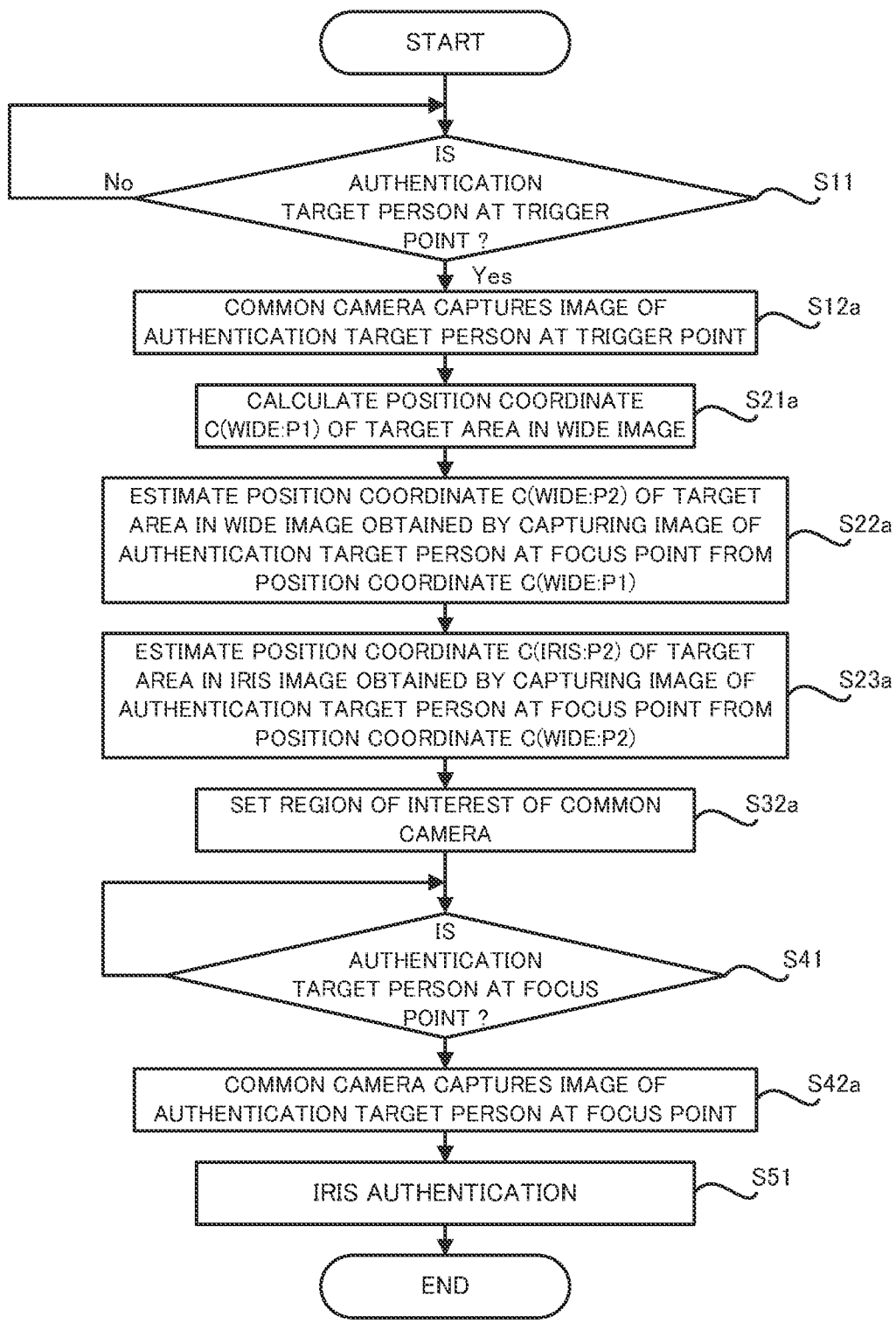
FIG. 10 is a flow chart that illustrates a flow of an operation of the iris authentication system (namely, an iris authentication operation) in the first modified example.

Next, with reference to FIG. 10, a flow of the operation (namely, the iris authentication operation) of the iris authentication system 1a in the first modified example will be described. FIG. 10 is a flow chart that illustrates the flow of the operation (namely, the iris authentication operation) of the iris authentication system 1a in the first modified example. Note that a detailed description of a process that is same as a process described in the above described FIG. 5 is omitted by assigning the same step number thereto.

As illustrated in FIG. 10, in the first modified example, when it is determined that the authentication target person T is located at the trigger point P1 (the step S1: Yes), the imaging control unit 615 controls the common camera 7a to capture the image of the authentication target person T located at the trigger point P1 (a step S12a). In this case, the imaging control unit 615 controls the common camera 7a so that the state of the common camera 7a becomes the wide imaging state before controlling the common camera 7a to capture the image of the authentication target person T located at the trigger point P1. For example, when the common camera 7a is provided with the optical system including the zoom lens as described above, the imaging control unit 615 controls the zoom lens (for example, moves a movable lens included in the zoom lens) so that the focal length of the optical system including the zoom lens is set to be the relatively short first distance. Then, the imaging control unit 615 controls the common camera 7a to capture the image of the authentication target person T located at the trigger point P1. As a result, the common camera 7a captures the image of the authentication target person T located at the trigger point P1 (the step S12a). The wide image 200(P1) captured by the common camera 7a is obtained by the image obtaining unit 611 (the step S12a).

Then, the area detection unit 612 detects, as the target area TA, an image part of the wide image 200(P1) in which the target portion TP is included by performing the image processing on the wide image 200(P1) obtained at the step S12a (the step S21). Furthermore, the area detection unit 612 calculates the position coordinate C of the detected target area TA in the wide image 200(P1) (the step S21).

Then, the coordinate estimation unit 613 estimates, on the basis of the position coordinate C(wide:P1) of the target area TA that is calculated at the step S21, the position coordinate C(wide:P2) of the target area TA in the wide image 200(P2) that is expected to be obtained under the assumption that the common camera 7a in the wide imaging state has captured the image of the authentication target person T that has moved from the trigger point P1 to the focus point P2 (a step S22a). Note that the coordinate estimation unit 613 may estimate the position coordinate C(wide:P2) from the position coordinate C(wide:P1) by using the first correspondence information that indicates the correspondence between the object included in the wide image 200(P1) and the same object included in the wide image 200(P2) at the step S22a, as with the above described step S22. However, the first correspondence information in the first modified example is different from the above described first correspondence information in that it is information targeting at the common camera 7a.

Then, the coordinate estimation unit 613 estimates, on the basis of the position coordinate C(wide:P2) that is estimated at the step S22, the position coordinate C(iris:P2) of the target area TA in the iris image 300 that is expected to be obtained under the assumption that the common camera 7a in the iris imaging state has captured the image of the authentication target person T that has moved from the trigger point P1 to the focus point P2 (a step S23a). Note that the coordinate estimation unit 613 may estimate the position coordinate C(iris:P2) from the position coordinate C(wide: P2) by using the second correspondence information that indicates the correspondence between the object included in the wide image 200(P2) and the same object included in the iris image 300(P2) at the step S23a, as with the above described step S23. However, the second correspondence information in the first modified example is different from the above described second correspondence information targeting at the wide camera 2 and the iris cameras 3 in that it is information targeting at the common camera 7a in the wide imaging state and the common camera 7a in the iris imaging state (especially, the common camera 7a in the iris imaging state that is configured to capture the image of the target portion TP of the authentication target person T located at the focus point P2). Incidentally, in the first modified example, since the common camera 7a is used instead of the plurality of iris cameras 3, the coordinate estimation unit 613 estimates, on the basis of the position coordinate C(wide:P2), the position coordinate C(iris:P2) of the target area TA in the iris image 300(P2) without performing a process of determining one iris image 300(P2) in which the target area TA is expected to be included from the plurality of iris images 300(P2).

Then, the camera set unit 614 sets, on the basis of the position coordinate C(iris:P2) that is estimated at the step S23, the region of interest (ROI: Region of Interest) IA that defines the image part, which is actually obtained (namely, read) for performing the iris authentication, of the iris image 300 captured by one common camera 7a in the iris imaging state (a step S32a). Note that the process at the step S32a may be same as the process at the above described step S32 that targets the iris camera 3, except that it targets at the common camera 7a.

Then, when it is determined that the authentication target person T is located at the focus point P2 (the step S41: Yes), the imaging control unit 615 controls the common camera 7a to capture the image of the authentication target person T located at the focus point P2 (a step S42a). In this case, the imaging control unit 615 controls the common camera 7a so that the state of the common camera 7a is switched from the wide imaging state to the iris imaging state before controlling the common camera 7a to capture the image of the authentication target person T located at the focus point P2. Specifically, the imaging control unit 615 controls the common camera 7a so that the state of the common camera 7a is switched from the wide imaging state to the iris imaging state before the iris image 300 is obtained at the step S42a after the wide image 200 is obtained at the step S12a. When the common camera 7a is provided with the optical system including the zoom lens as described above, the imaging control unit 615 controls the zoom lens (for example, moves the movable lens included in the zoom lens) so that the focal length of the optical system including the zoom lens is set to be the relatively long second distance. Namely, the imaging control unit 615 changes the focal length of the optical system including the zoom lens from the relatively short first distance to the relatively long second distance. As a result, the state of the common camera 7a is switched from the wide imaging state to the iris imaging state. Then, the imaging control unit 615 controls the common camera 7a to capture the image of the authentication target person T located at the focus point P2. As a result, the common camera 7a captures the image of the authentication target person T located at the focus point P2 (the step S42a). The iris image 300 captured by the common camera 7a (especially, the image part of the iris image 300 in the region of interest IA) is obtained by the image obtaining unit 611 (the step S42a).

Then, the authentication unit 616 performs the iris authentication by using the iris image 300 obtained at the step S42 (the step S51).

The iris authentication system 1a in the first modified example described above is able to achieve an effect that is same as an effect achievable by the above described iris authentication system 1.

(4-2) Other Modified Example

In the above described description, the coordinate estimation unit 613 estimates the position coordinate C(wide: P2) from the position coordinate C(wide:P1) and then estimates the position coordinate C(iris:P2) from the position coordinate C(wide:P2) by using two correspondence information, the first and second correspondence information. However, the coordinate estimation unit 613 may estimate the position coordinate C(iris:P2) directly from the position coordinate C(wide:P1) by using single correspondence information to which both of the first and second correspondence information are reflected (for example, single transformation matrix that corresponds to the first transformation matrix H1×the second transformation matrix H2. Even in this case, an operation for estimating the position coordinate C(iris:P2) directly from the position coordinate C(wide:P1) is equivalent to an operation for estimating the position coordinate C(wide:P2) from the position coordinate C(wide: P1) and then estimating the position coordinate C(iris:P2)

from the position coordinate C(wide:P2), as long as the first correspondence information is reflected to the single correspondence information.

In the above described description, single trigger point P1 is set. However, a plurality of trigger points P1 distances from the reference point P0 of which are different from each other may be set. In this case, the wide camera 2 may capture the image of the authentication target person T located at at least one trigger point P1 of the plurality of trigger points P1. Alternatively, the iris authentication system 1 may be provided with a plurality of wide cameras 2 that correspond to the plurality of trigger points P1, respectively. Moreover, when the plurality of trigger points P1 are set, the iris authentication system 1 may be provided with a plurality of human detection sensors 4 that correspond to the plurality of trigger points P1, respectively.

The iris authentication system 1 may be provided with single iris camera 3. In this case, the range of the field of view of the iris camera 3 may be set to be a proper range so that the iris camera 3 is configured to capture the image of the target portion TP of the authentication target person T located at the focus point P2 regardless of the height of the authentication target person T. Moreover, when the iris authentication system 1 is provided with single iris camera 3, the camera set unit 614 may not perform the process at the step S31 of FIG. 5 (namely, the process of selecting one iris camera 3 that captures the image of the authentication target person T).

The camera set unit 614 may not perform the process of setting the region of interest IA (the process corresponding to the step S32 of FIG. 5 or the step S32a of FIG. 10). In this case, the iris authentication system 1 may not operates in the region of interest mode. Specifically, the image obtaining unit 611 may obtain whole of the iris image 300 captured by the iris camera 3 or the common camera 7a. The authentication unit 616 may perform the iris authentication by using whole of the iris image 300 captured by the iris camera 3 or the common camera 7a.

Figure 11:
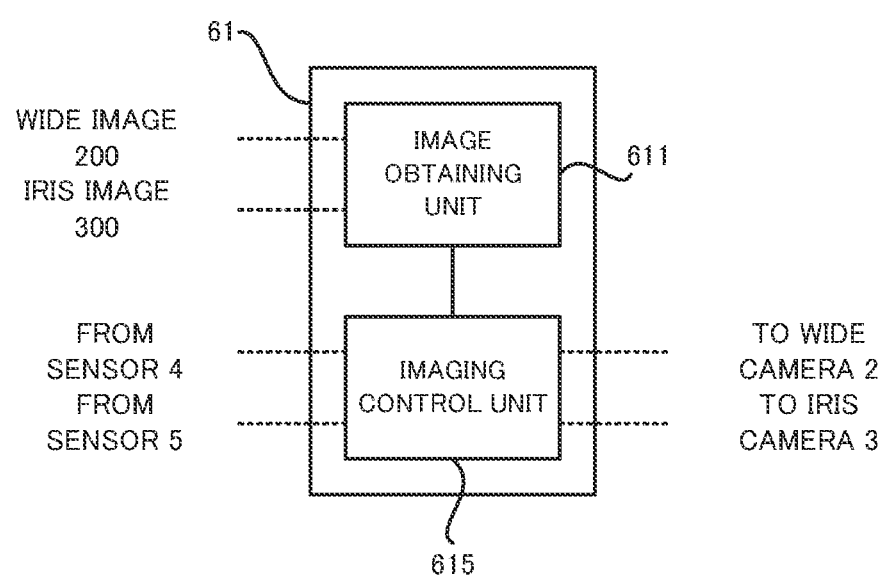
FIG. 11 is a block diagram that illustrates a modified example of the functional block implemented in the CPU of the iris authentication apparatus.

In the above described description, the iris authentication apparatus 6 is provided with the image obtaining unit 611, the area detection unit 612, the coordinate estimation unit 613, the camera set unit 614, the imaging control unit 615 and the authentication unit 616. However, as illustrated in FIG. 11 that is a block diagram illustrating a modified example of the iris authentication apparatus 6, the iris authentication apparatus 6 may not be provided with at least one of the area detection unit 612, the coordinate estimation unit 613 and the camera set unit 614. In this case, the imaging control unit 615 may perform the process that is performed by each of the area detection unit 612, the coordinate estimation unit 613 and the camera set unit 614. Alternatively, an apparatus outside the iris authentication apparatus 6 may perform the process that is performed by each of the area detection unit 612, the coordinate estimation unit 613 and the camera set unit 614. Moreover, as illustrated in FIG. 11, the iris authentication apparatus 6 may not be provided with the authentication unit 616. In this case, an apparatus outside the iris authentication apparatus 6 may perform the process that is performed by the authentication unit 616.

In the above described description, the iris authentication system 1 is provided with the human detection sensor 4. However, the iris authentication system 1 may not be provided with the human detection sensor 4. In this case, the wide camera 2 or the common camera 7a may keep capturing the image of the scene in the range of the field of view at a predetermined frame rate (namely, an imaging rate) regardless of whether the authentication target person T is located at the trigger point P1. Typically, the wide camera 2 or the common camera 7a may keep capturing the image of the scene in the range of the field of view at the predetermined frame rate during at least a period when the authentication target person T passes through the trigger point P1. As a result, even when the iris authentication system 1 is not provided with the human detection sensor 4, the wide camera 2 or the common camera 7a is able to capture the image of the authentication target person T at a timing when the authentication target person T reaches the trigger point P1. Namely, even when the iris authentication system 1 is not provided with the human detection sensor 4, the image obtaining unit 611 is able to obtain the wide image 200 including the authentication target person T located at the trigger point P1.

When the iris authentication system 1 is not provided with the human detection sensor 4, the iris authentication apparatus 6 (for example, the area detection unit 612) may determine whether or not the wide image 200 including the authentication target person T located at the trigger point P1 is obtained by performing an image analysis on the wide image 200. Namely, the iris authentication apparatus 6 may determine whether or not the authentication target person T is located at the trigger point P1 by performing the image analysis on the wide image 200. When it is determined that the authentication target person T is located at the trigger point P1 (namely, the wide image 200 including the authentication target person T located at the trigger point P1 is obtained), the iris authentication apparatus 6 performs the process of selecting one iris camera 3 for capturing the image of the authentication target person T located at the focus point P2 (specifically, a series of processes from the step S21 to the step S32 of FIG. 5 or FIG. 10) on the basis of the wide image 200. On the other hand, when it is determined that the authentication target person T is not located at the trigger point P1, the iris authentication apparatus 6 does not start a series of processes from the step S21 to the step S32 of FIG. 5 or FIG. 10. Note that the iris authentication apparatus 6 may use an existing method as a method for the image analysis for determining whether or not the authentication target person T is located at the trigger point P1. For example, the iris authentication apparatus 6 may determine whether or not the authentication target person T is located at the trigger point P1 by estimating a depth from the wide image 200. For example, the iris authentication apparatus 6 may determine whether or not the authentication target person T is located at the trigger point P1 by detecting a foot of the authentication target person T included in the wide image 200 and determining whether or not the detected foot is located at the trigger point P1. For example, the iris authentication apparatus 6 may determine whether or not the authentication target person T is located at the trigger point P1 by determining whether or not an interval between both eyes of the authentication target person T included in the wide image 200 is a predetermined value.

In the above described description, the iris authentication system 1 is provided with the human detection sensor 5. However, the iris authentication system 1 may not be provided with the human detection sensor 5. In this case, the iris camera 3 on which the region of interest IA is already set may keep capturing the image of the scene in the range of the field of view at a predetermined frame rate (namely, an imaging rate) regardless of whether the authentication target person T is located at the focus point P2 after the region of interest IA of the iris camera 3 is set at the step S32 of FIG.

5. Alternatively, the common camera 7a on which the region of interest IA is already set may keep capturing the image of the scene in the range of the field of view at a predetermined frame rate (namely, an imaging rate) regardless of whether the authentication target person T is located at the focus point P2 after the region of interest IA of the common camera 7a is set at the step S32a of FIG. 10. Typically, the iris camera 3 or the common camera 7a may keep capturing the image of the scene in the range of the field of view at the predetermined frame rate (namely, the imaging rate) during at least a period when the authentication target person T passes through the focus point P2. As a result, even when the iris authentication system 1 is not provided with the human detection sensor 5, the iris camera 3 or the common camera 7a is able to capture the image of the authentication target person T at a timing when the authentication target person T reaches the focus point P2 from the trigger point P1. Namely, even when the iris authentication system 1 is not provided with the human detection sensor 5, the image obtaining unit 611 is able to obtain the iris image 300 including the authentication target person T located at the focus point P2.

In the above described description, the example embodiment of the imaging system, the imaging method, the control apparatus, the computer program and the recording medium is applied to the iris authentication system 1. However, the example embodiment of the imaging system, the imaging method, the control apparatus, the computer program and the recording medium may be applied to any authentication system that performs an authentication of the authentication target person T on the basis of a feature of a predetermined part of the authentication target person T that is different from the iris. Namely, the iris authentication system 1 may be modified to be any authentication system that performs any authentication operation. A face authentication system that performs the authentication of the authentication target person T on the basis of a feature of a face of the authentication target person T is one example of any authentication system. Alternatively, the example embodiment of the imaging system, the imaging method, the control apparatus, the computer program and the recording medium may be applied to any imaging system that controls the iris camera 3 (alternatively, a second imaging apparatus) to capture an image of a moving imaging target person on the basis of an image of the imaging target person captured by the wide camera 2 (alternatively, a first imaging apparatus). Namely, the iris authentication system 1 may be modified to be any imaging system that captures the image of the imaging target person at the above described trigger point P1 and the focus point P2 by using at least two types of imaging apparatuses, respectively.

The iris authentication system 1 may authenticate the authentication target person T by using any part of the authentication target person T in addition to or instead of authenticating the authentication target person T by using the iris of the authentication target person T. Namely, any authentication system that authenticates the authentication target person T by using any part of the authentication target person T may have a configuration and performs an operation that are same as those of the iris authentication system 1. A face authentication system that authenticates the authentication target person T by using the face of the authentication target person T is one example of any authentication system.

(5) SUPPLEMENTARY NOTE

With respect to the example embodiments described above, the following Supplementary Notes will be further disclosed.

(5-1) Supplementary Note 1

An imaging system according to a supplementary note 1 is an imaging system that is provided with:
a first imaging apparatus that captures an image of an imaging target that is located at a first point;
a second imaging apparatus a focus position of which is set at a second point that is located at a forward side along a moving direction of the imaging target than the first point; and
a control apparatus that controls the second imaging apparatus to capture an image of the imaging target that is located at the second point on the basis of the image captured by the first imaging apparatus.

(5-2) Supplementary Note 2

An imaging system according to a supplementary note 2 is the imaging system according to the supplementary note 1 that is further provided with:
a first detection apparatus that detects whether or not the imaging target is located at the first point; and
a second detection apparatus that detects whether or not the imaging target is located at the second point.

(5-3) Supplementary Note 3

An imaging system according to a supplementary note 3 is the imaging system according to the supplementary note 2, wherein
the first imaging apparatus captures the image of the imaging target that is located at the first point when the first detection apparatus detects that the imaging target is located at the first point,
the second imaging apparatus captures the image of the imaging target that is located at the second point when the second detection apparatus detects that the imaging target is located at the second point.

(5-4) Supplementary Note 4

An imaging system according to a supplementary note 4 is the imaging system according to the supplementary note 1, wherein
the second imaging apparatus keeps capturing the image at a desired imaging rate during a period when the imaging target passes through the second point.

(5-5) Supplementary Note 5

An imaging system according to a supplementary note 5 is the imaging system according to the supplementary note 1 or 4 that is further provided with a first detection apparatus that detects whether or not the imaging target is located at the first point,
the first imaging apparatus captures the image of the imaging target that is located at the first point when the first detection apparatus detects that the imaging target is located at the first point.

(5-6) Supplementary Note 6

An imaging system according to a supplementary note 6 is the imaging system according to any one of the supplementary notes 1 to 5, wherein
the control apparatus (i) determines, on the basis of the image captured by the first imaging apparatus, a first position that is a position of the imaging target located at the first point in the image captured by the first imaging apparatus, (ii) estimates, on the basis of the first position, a second position that is a position of the imaging target in the image captured by the second imaging apparatus under the assumption that the second imaging apparatus has captured the image of the imaging target that has moved from the first point to the second point, and (iii) controls, on the basis of the second position, the second imaging apparatus to capture the image of the imaging target that is located at the second point.

(5-7) Supplementary Note 7

An imaging system according to a supplementary note 7 is the imaging system according to the supplementary note 6, wherein
in order to estimate the second position on the basis of the first position, the control apparatus (i) estimates, on the basis of the first position, a third position that is a position of the imaging target in the image captured by the first imaging apparatus under the assumption that the first imaging apparatus has captured the image of the imaging target that has moved from the first point to the second point, and (ii) estimates the second position on the basis of the third position.

(5-8) Supplementary Note 8

An imaging system according to a supplementary note 8 is the imaging system according to any one of the supplementary notes 1 to 7 that is provided with a plurality of second imaging apparatuses,
the control apparatus determines, from the image captured by the first imaging apparatus, a position of the imaging target in the image, and selects, on the basis of the determined position, one second imaging apparatus that captures the image of the imaging target that is located at the second point.

(5-9) Supplementary Note 9

An imaging system according to a supplementary note 9 is the imaging system according to the supplementary note 7, wherein
the control apparatus estimates the third position on the basis of the first position and information relating to the moving direction of the imaging target.

(5-10) Supplementary Note 10

An imaging system according to a supplementary note 10 is the imaging system according to any one of the supplementary notes 1 to 9, wherein
the control apparatus controls the second imaging apparatus to capture the image of the imaging target that is located at the second point on the basis of the image captured by the first imaging apparatus and information relating to the moving direction of the imaging target.

(5-11) Supplementary Note 11

An imaging system according to a supplementary note 11 is the imaging system according to the supplementary note 9 or 10, wherein
the information relating to the moving direction of the imaging target includes a correspondence relationship between a position of an object in the image captured by the first imaging apparatus under the assumption that the first imaging apparatus has captured the image of the object that is located at the first point and a position of the object in the image captured by the first imaging apparatus under the assumption that the first imaging apparatus has captured the image of the object that is located at the second point.

(5-12) Supplementary Note 12

An imaging system according to a supplementary note 12 is the imaging system according to any one of the supplementary notes 1 to 11 that is provided with a plurality of second imaging apparatuses,
the control apparatus selects, on the basis of the image captured by the first imaging apparatus, one second imaging apparatus that should capture the image of the imaging target that is located at the second point among the plurality of second imaging apparatuses, and controls the selected one second imaging apparatus to captures the image of the imaging target that is located at the second point (5-13) Supplementary Note 13

An imaging system according to a supplementary note 13 is the imaging system according to any one of the supplementary notes 1 to 12, wherein
a plurality of first points are set,
the first imaging apparatus captures the image of the imaging target that is located at at least one of the plurality of first points.

(5-14) Supplementary Note 14

An imaging system according to a supplementary note 14 is an imaging system that is provided with:
an imaging apparatus a state of which is switchable between a first state and a second state, that captures an image of an imaging target that is located at a first point in the first state, and that captures an image of the imaging target that is located at a second point, which is located at a forward side along a moving direction of the imaging target than the first point, in the second state; and
a control apparatus that switches the imaging apparatus from the first state to the second state by controlling the imaging apparatus on the basis of the image captured by the imaging apparatus in the first state.

(5-15) Supplementary Note 15

An imaging system according to a supplementary note 15 is the imaging system according to the supplementary note 14, wherein the imaging apparatus sets a focus position in an area including the first point in the first state and sets the focus position in an area including the second point in the second state.

(5-16) Supplementary Note 16

An imaging system according to a supplementary note 16 is the imaging system according to the supplementary note 14 or 15 that is further provided with:
a first detection apparatus that detects whether or not the imaging target is located at the first point; and
a second detection apparatus that detects whether or not the imaging target is located at the second point.

(5-17) Supplementary Note 17

An imaging system according to a supplementary note 17 is the imaging system according to the supplementary note 16, wherein
the imaging apparatus in the first state captures the image of the imaging target that is located at the first point when the first detection apparatus detects that the imaging target is located at the first point,
the imaging apparatus in the second state captures the image of the imaging target that is located at the second point when the second detection apparatus detects that the imaging target is located at the second point.

(5-18) Supplementary Note 18

An imaging system according to a supplementary note 18 is the imaging system according to any one of the supplementary notes 14 to 17, wherein
the imaging apparatus keeps capturing the image at a desired imaging rate during a period when the imaging target passes through the second point.

(5-19) Supplementary Note 19

An imaging system according to a supplementary note 19 is the imaging system according to the supplementary note 14, 15 or 18 that is further provided with a first detection apparatus that detects whether or not the imaging target is located at the first point,
the imaging apparatus captures the image of the imaging target that is located at the first point when the first detection apparatus detects that the imaging target is located at the first point.

(5-20) Supplementary Note 20

An imaging system according to a supplementary note 20 is the imaging system according to any one of the supplementary notes 14 to 19, wherein
the control apparatus (i) determines, on the basis of the image captured by the imaging apparatus in the first state, a first position that is a position of the imaging target located at the first point in the image captured by the imaging apparatus in the first state, (ii) estimates, on the basis of the first position, a second position that is a position of the imaging target in the image captured by the imaging apparatus in the second state under the assumption that the imaging apparatus in the second state has captured the image of the imaging target that has moved from the first point to the second point, and (iii) controls, on the basis of the second position, the imaging apparatus in the second state to capture the image of the imaging target that is located at the second point.

(5-21) Supplementary Note 21

An imaging system according to a supplementary note 21 is the imaging system according to the supplementary note 20, wherein
in order to estimate the second position on the basis of the first position, the control apparatus (i) estimates, on the basis of the first position, a third position that is a position of the imaging target in the image captured by the imaging apparatus in the first state under the assumption that the imaging apparatus in the first state has captured the image of the imaging target that has moved from the first point to the second point, and (ii) estimates the second position on the basis of the third position.

(5-22) Supplementary Note 22

An imaging system according to a supplementary note 22 is the imaging system according to the supplementary note 21, wherein
the control apparatus estimates the third position on the basis of the first position and information relating to the moving direction of the imaging target.

(5-23) Supplementary Note 23

An imaging system according to a supplementary note 23 is the imaging system according to any one of the supplementary notes 13 to 22, wherein
the control apparatus controls the imaging apparatus in the second state to capture the image of the imaging target that is located at the second point on the basis of the image captured by the imaging apparatus in the first state and information relating to the moving direction of the imaging target.

(5-24) Supplementary Note 24

An imaging system according to a supplementary note 24 is the imaging system according to the supplementary note 22 or 23, wherein
the information relating to the moving direction of the imaging target includes a correspondence relationship between a position of an object in the image captured by the imaging apparatus in the first under the assumption that the imaging apparatus in the first state has captured the image of the object that is located at the first point and a position of the object in the image captured by the imaging apparatus in the first state under the assumption that the imaging apparatus in the first state has captured the image of the object that is located at the second point.

(5-25) Supplementary Note 25

An imaging system according to a supplementary note 25 is the imaging system according to any one of the supplementary notes 14 to 24, wherein
a plurality of first points are set,
the imaging apparatus in the first state captures the image of the imaging target that is located at at least one of the plurality of first points.

(5-26) Supplementary Note 26

An imaging method according to a supplementary note 26 is an imaging method including:
  an obtaining step that obtains an image captured by a first imaging apparatus that captures an image of an imaging target that is located at a first point; and
  a controlling step that controls, on the basis of the image obtained at the obtaining step, a second imaging apparatus a focus position of which is set at a second point to capture an image of the imaging target located at the second point that is located at a forward side along a moving direction of the imaging target than the first point.

(5-27) Supplementary Note 27

An imaging method according to a supplementary note 27 is an imaging method including:
  an obtaining step that obtains an image captured by an imaging apparatus in a first state from the imaging apparatus a state of which is switchable between the first state and a second state, that captures an image of an imaging target that is located at a first point in the first state, and that captures an image of the imaging target that is located at a second point, which is located at a forward side along a moving direction of the imaging target than the first point, in the second state; and
  a controlling step that switches the imaging apparatus from the first state to the second state by controlling the imaging apparatus on the basis of the image obtained at the obtaining step.

(5-28) Supplementary Note 28

A control apparatus according to a supplementary note 28 is a control apparatus that is provided with:
  an obtaining unit that obtains an image captured by a first imaging apparatus that captures an image of an imaging target that is located at a first point; and
  a controlling unit that controls, on the basis of the image obtained by the obtaining unit, a second imaging apparatus a focus position of which is set at a second point to capture an image of the imaging located at the second point that is located at a forward side along a moving direction of the imaging target than the first point.

(5-29) Supplementary Note 29

A control apparatus according to a supplementary note 29 is a control apparatus that is provided with:
  an obtaining unit that obtains an image captured by an imaging apparatus in a first state from the imaging apparatus a state of which is switchable between the first state and a second state, that captures an image of an imaging target that is located at a first point in the first state, and that captures an image of the imaging target that is located at a second point, which is located at a forward side along a moving direction of the imaging target than the first point, in the second state; and
  a controlling unit that switches the imaging apparatus from the first state to the second state by controlling the imaging apparatus on the basis of the image obtained by the obtaining unit.

(5-30) Supplementary Note 30

A computer program described in a Supplementary Note 30 is a computer program that allows a computer to execute the imaging method described in the Supplementary Note 26 or 27.

(5-31) Supplementary Note 31

A recording medium described in a Supplementary Note 31 is a recording medium on which the computer program described in the Supplementary Note 30 is recorded.

This disclosure is allowed to be changed, if desired, without departing from the essence or spirit of the invention which can be read from the claims and the entire specification, and an imaging system, an imaging method, a control apparatus, a computer program and a recording medium, which involve such changes, are also intended to be within the technical scope of this disclosure.

DESCRIPTION OF REFERENCE CODES 1 iris authentication system
2 wide camera
200 wide image
3 iris camera
300 iris image
4, 5 human detection sensor
6 iris authentication apparatus
61 CPU
611 image obtaining unit
612 area detection unit
613 coordinate estimation unit
614 camera set unit
615 imaging control unit
616 authentication unit
7a common camera
P1 trigger point
P2 focus point

The invention claimed is:

1. An imaging system comprising:
  a first imager that captures an image of an imaging target when the imaging target is located at a first point;
  a plurality of second imagers, a focus position of which is set at a second point that is located at a different position from the first point; and
  a controller that is programmed to control the second imagers to capture an image of the imaging target when the imaging target is located at the second point on the basis of the image captured by the first imager, wherein
  the controller is programmed to determine, on the basis of the image captured by the first imager, a first position that is a position of the imaging target located at the first point in the image captured by the first imager, estimate, on the basis of the first position, a second position that is a position of the imaging target in the image captured by the second imager under the assumption that the second imagers have captured the image of the imaging target after having moved from the first point to the second point, and select, on the basis of the second position, one second imager that captures the image of the imaging target when the imaging target is located at the second point.

2. The imaging system according to claim 1, wherein the second point that is located at a forward side after the first point, along a moving direction of the imaging target.

3. The imaging system according to claim 1, further comprising:
   a first detector that detects whether or not the imaging target is located at the first point; and
   a second detector that detects whether or not the imaging target is located at the second point.

4. The imaging system according to claim 3, wherein
   the first imager captures the image of the imaging target that is located at the first point when the first detector detects that the imaging target is located at the first point,
   the one second imager captures the image of the imaging target that is located at the second point when the second detector detects that the imaging target is located at the second point.

5. The imaging system according to claim 1, wherein
   the one second imager keeps capturing the image at a desired imaging rate during a period when the imaging target passes through the second point.

6. The imaging system according to claim 1 further comprising a first detector that detects whether or not the imaging target is located at the first point,
   the first imager capturing the image of the imaging target when the first detector detects that the imaging target is located at the first point.

7. The imaging system according to claim 1, wherein
   in order to estimate the second position on the basis of the first position, the controller is programmed to (i) estimate, on the basis of the first position, a third position that is a position of the imaging target in the image captured by the first imager under the assumption that the first imager has captured the image of the imaging target that has moved from the first point to the second point, and (ii) estimate, on the basis of the third position, the second position that is the position of the imaging target in the image captured by the second imagers under the assumption that the second imagers have captured the image of the imaging target that has moved from the first point to the second point.

8. An imaging method performed by a computer and comprising:
   obtaining an image captured by a first imager that captures an image of an imaging target when the imaging target is located at a first point;
   determining, on the basis of the image captured by the first imager, a first position that is a position of the imaging target located at the first point in the image captured by the first imager;
   estimating, on the basis of the first position, a second position that is a position of the imaging target in the image captured by a plurality of second imagers under the assumption that the second imagers have captured the image of the imaging target after having moved from the first point to a second point, wherein a focus position of the second imagers is set at the second point located at a different position from the first point; and
   selecting, on the basis of the second position, one second imager that captures the image of the imaging target when the imaging target is located at the second point.

9. A non-transitory recording medium storing a computer program executable by a computer to perform an imaging method comprising:
   obtaining an image captured by a first imager that captures an image of an imaging target when the imaging target is located at a first point;
   determining, on the basis of the image captured by the first imager, a first position that is a position of the imaging target located at the first point in the image captured by the first imager;
   estimating, on the basis of the first position, a second position that is a position of the imaging target in the image captured by a plurality of second imagers under the assumption that the second imagers have captured the image of the imaging target after having moved from the first point to a second point, wherein a focus position of the second imagers is set at the second point located at a different position from the first point; and
   selecting, on the basis of the second position, one second imager that captures the image of the imaging target when the imaging target is located at the second point.

* * * * *